(12) United States Patent
Hayes et al.

(10) Patent No.: US 12,121,211 B2
(45) Date of Patent: Oct. 22, 2024

(54) GUIDEWIRE AND CATHETER SYSTEM FOR IN-VIVO FORWARD VIEWING OF THE VASCULATURE

(71) Applicant: Lake Region Manufacturing, Inc., Chaska, MN (US)

(72) Inventors: John Michael Hayes, Cork (IE); Ivan Mooney, Tuam (IE)

(73) Assignee: Lake Region Manufacturing, Inc., Chaska, MN (US)

( * ) Notice: Subject to any disclaimer, the term of this patent is extended or adjusted under 35 U.S.C. 154(b) by 960 days.

(21) Appl. No.: 16/953,515

(22) Filed: Nov. 20, 2020

(65) Prior Publication Data
US 2021/0153725 A1 May 27, 2021

Related U.S. Application Data

(60) Provisional application No. 62/939,163, filed on Nov. 22, 2019.

(51) Int. Cl.
*A61B 1/05* (2006.01)
*A61B 1/00* (2006.01)
(Continued)

(52) U.S. Cl.
CPC ...... *A61B 1/00096* (2013.01); *A61B 1/00101* (2013.01); *A61B 1/00114* (2013.01);
(Continued)

(58) Field of Classification Search
None
See application file for complete search history.

(56) References Cited

U.S. PATENT DOCUMENTS

| 5,940,126 A * | 8/1999 | Kimura | H04N 25/41 |
| | | | 348/E5.028 |
| 6,887,196 B2 * | 5/2005 | Arai | A61B 1/00096 |
| | | | 600/177 |

(Continued)

FOREIGN PATENT DOCUMENTS

| WO | 2007038787 A1 | 4/2007 |
| WO | 2016160967 A1 | 10/2016 |
| WO | 2019/138220 A1 | 7/2019 |

OTHER PUBLICATIONS

"Extended European Search Report Dated Feb. 12, 2021, Application No. 20209203.7".

(Continued)

*Primary Examiner* — John P Leubecker
(74) *Attorney, Agent, or Firm* — Michael F. Scalise

(57) ABSTRACT

A medical system comprising a guidewire that is connectable to a catheter is described. The guidewire has a housing connected to the distal end of a core wire. A printed circuit board (PCB) electrically connected to a camera chip resides in the housing. An atraumatic lens is supported by the housing with the camera chip residing between the atraumatic lens and the housing so that light rays entering the atraumatic lens are refracted to a focal plane aligned along a distal face of the camera chip. A proximal connector powered by a controller is wired to a visual display. With the proximal end of the guidewire connected to the proximal connector, the controller provides electrical power to the camera chip via a power cable extending along the core wire to the PCB. The catheter has an axially-extending primary lumen and a plurality of optical fibers extending to respective light-emitting lenses. During a medical procedure, the guidewire is first inserted into the vasculature of a patient. The guidewire is then received in the primary lumen of the catheter to connect the catheter to the guidewire. Then, the
(Continued)

guidewire is connected to the proximal connector to enable the controller to provide electrical power to the camera chip. This provides the surgeon with a visual image of the vasculature illuminated by the light-emitting lenses of the catheter during the medical procedure.

21 Claims, 16 Drawing Sheets

(51) Int. Cl.
    *A61B 1/06*       (2006.01)
    *A61B 1/07*       (2006.01)
    *A61B 1/313*      (2006.01)
    *A61M 25/09*     (2006.01)
    *G02B 3/00*       (2006.01)
    *G02B 9/10*       (2006.01)
    *G02B 27/30*      (2006.01)
    *H04N 23/54*     (2023.01)
    *H04N 23/55*     (2023.01)
    *H04N 23/50*     (2023.01)

(52) U.S. Cl.
    CPC .......... *A61B 1/00128* (2013.01); *A61B 1/051* (2013.01); *A61B 1/0607* (2013.01); *A61B 1/07* (2013.01); *A61B 1/3137* (2013.01); *A61M 25/09* (2013.01); *G02B 3/0087* (2013.01); *G02B 9/10* (2013.01); *G02B 27/30* (2013.01); *H04N 23/54* (2023.01); *H04N 23/55* (2023.01); *A61M 2025/09091* (2013.01); *A61M 2025/09175* (2013.01); *G02B 2003/0093* (2013.01); *H04N 23/555* (2023.01)

(56) References Cited

U.S. PATENT DOCUMENTS

| | | | |
|---|---|---|---|
| 7,030,926 B2 * | 4/2006 | Miyake | H04N 23/58 348/14.02 |
| 7,396,354 B2 | 7/2008 | Rychnovsky et al. | |
| 7,625,335 B2 | 12/2009 | Deichmann et al. | |
| 8,657,811 B2 | 2/2014 | Arai et al. | |
| 8,803,960 B2 | 8/2014 | Sonnenschein et al. | |
| 9,084,611 B2 | 7/2015 | Amirana et al. | |
| 10,080,484 B2 | 9/2018 | Yang et al. | |
| 10,433,710 B1 | 10/2019 | Griffin | |
| 10,448,815 B2 | 10/2019 | Jung et al. | |
| 2001/0039371 A1 * | 11/2001 | Forster | G02B 23/2446 600/176 |
| 2002/0003660 A1 * | 1/2002 | Abe | G02B 27/0056 359/566 |
| 2003/0028078 A1 | 2/2003 | Glukhovsky | |
| 2003/0222325 A1 * | 12/2003 | Jacobsen | A61B 1/05 257/434 |
| 2004/0092830 A1 | 5/2004 | Scott et al. | |
| 2004/0147806 A1 | 7/2004 | Adler | |
| 2008/0080060 A1 * | 4/2008 | Messerschmidt | G02B 23/2407 359/654 |
| 2008/0173792 A1 * | 7/2008 | Yang | H01L 27/14636 250/208.1 |
| 2008/0214940 A1 | 9/2008 | Benaron et al. | |
| 2008/0255416 A1 * | 10/2008 | Gilboa | A61B 1/055 600/110 |
| 2008/0262295 A1 * | 10/2008 | Kendale | A61B 1/00096 600/153 |
| 2009/0306477 A1 * | 12/2009 | Togino | G02B 13/06 600/176 |
| 2010/0081873 A1 * | 4/2010 | Tanimura | A61B 1/00165 600/109 |
| 2013/0231533 A1 | 9/2013 | Papademetriou et al. | |
| 2015/0015687 A1 * | 1/2015 | Adler | A61B 1/00096 29/428 |
| 2015/0202089 A1 | 7/2015 | Campbell et al. | |
| 2016/0045101 A1 * | 2/2016 | Nakatate | A61B 1/00078 600/478 |
| 2018/0070803 A1 * | 3/2018 | Mikami | A61B 1/00096 |
| 2019/0070395 A1 | 3/2019 | Govari et al. | |
| 2019/0133423 A1 * | 5/2019 | Birnkrant | A61B 1/04 |
| 2019/0150718 A1 | 5/2019 | Melsky | |
| 2019/0167081 A1 | 6/2019 | Hillman | |
| 2019/0298451 A1 | 10/2019 | Wong et al. | |
| 2020/0008659 A1 * | 1/2020 | Viebach | A61B 1/00174 |
| 2020/0297203 A1 * | 9/2020 | Togino | A61B 1/0607 |
| 2022/0240768 A1 * | 8/2022 | Watanabe | A61B 1/0005 |

OTHER PUBLICATIONS

"Extended European Search Report Dated Nov. 12, 2020, Application No. 20187972.3".

* cited by examiner

GUIDEWIRE AND CATHETER SYSTEM FOR IN-VIVO FORWARD VIEWING OF THE VASCULATURE

CROSS-REFERENCE TO RELATED APPLICATION

This application claims priority to U.S. Provisional Application Ser. No. 62/939,163, filed on Nov. 22, 2019.

BACKGROUND OF THE INVENTION

1. Field of the Invention

The present invention relates to the art of delivering medical therapy to a remote site in a body. More particularly, the present invention relates to a video camera equipped guidewire that extends through the lumen of a light-illuminating catheter. The guidewire and catheter are moved through the vasculature together. The catheter has optical fibers that illuminate the path forward through the vasculature while the camera in the catheter sends a video feed back to a controller connected to a video display.

2. Prior Art

The current gold standard for imaging during interventional procedures is fluoroscopy. However, fluoroscopy gives 2D greyscale images which require a significant amount of interpretation from the surgeon. This both slows down the procedure and adds to its difficulty. Also, other than giving 2D dimensions, fluoroscopy provides limited information about the diseased area.

Another problem with fluoroscopy is that it is relatively dangerous. According to the FDA, fluoroscopy can result in relatively high radiation doses, especially for complex interventional procedures such as placing stents or other devices inside the body. These types of interventional procedures require that fluoroscopy be administered for a relatively long period of time. Radiation-related risks associated with fluoroscopy include: radiation-induced injuries to the skin and underlying tissues ("burns"), which occur shortly after the exposure, and radiation-induced cancers, which may occur sometime later in life.

SUMMARY OF THE INVENTION

To overcome these issues, the present invention combines a guidewire that is equipped with a video camera in its atraumatic head with a light-illuminating catheter. The catheter has an array of light-emitting lenses connected to optical fibers. With the guidewire residing in the catheter lumen, the atraumatic head of the guidewire is positioned a short distance ahead or distal the light-emitting lenses of the catheter. With the video camera in the atraumatic head of the guidewire sending a real-time video feed of the vasculature back to the surgeon, the surgeon is better able to control the directional movement of the catheter/guidewire system through the vasculature. That is done by manipulating the guidewire using a series of pull-wires so that the catheter is bent into a directional orientation in anticipation of the viewed route of the vasculature immediately ahead. This helps to reduce trauma to the vasculature as there is not as much contact with the vasculature as there might be without video viewing.

Moreover, once the catheter/guidewire system has reached the body tissue of interest in the vasculature, the video camera enables the surgeon to access the diseased tissue faster and more accurately, which helps the surgeon decide in a treatment protocol faster than when using a system without light-assisted video viewing. Further, once a treatment has been deployed, for example, a stent has been placed in the vasculature to open an occlusion, the catheter/guidewire system of the present invention helps in in situ assessment of proper stent placement and treatment efficacy.

These and other objects of the present invention will become increasingly more apparent to those skilled in the art by reference to the following detailed description and to the appended drawings.

DETAILED DESCRIPTION OF THE PREFERRED EMBODIMENTS

Figure 1:
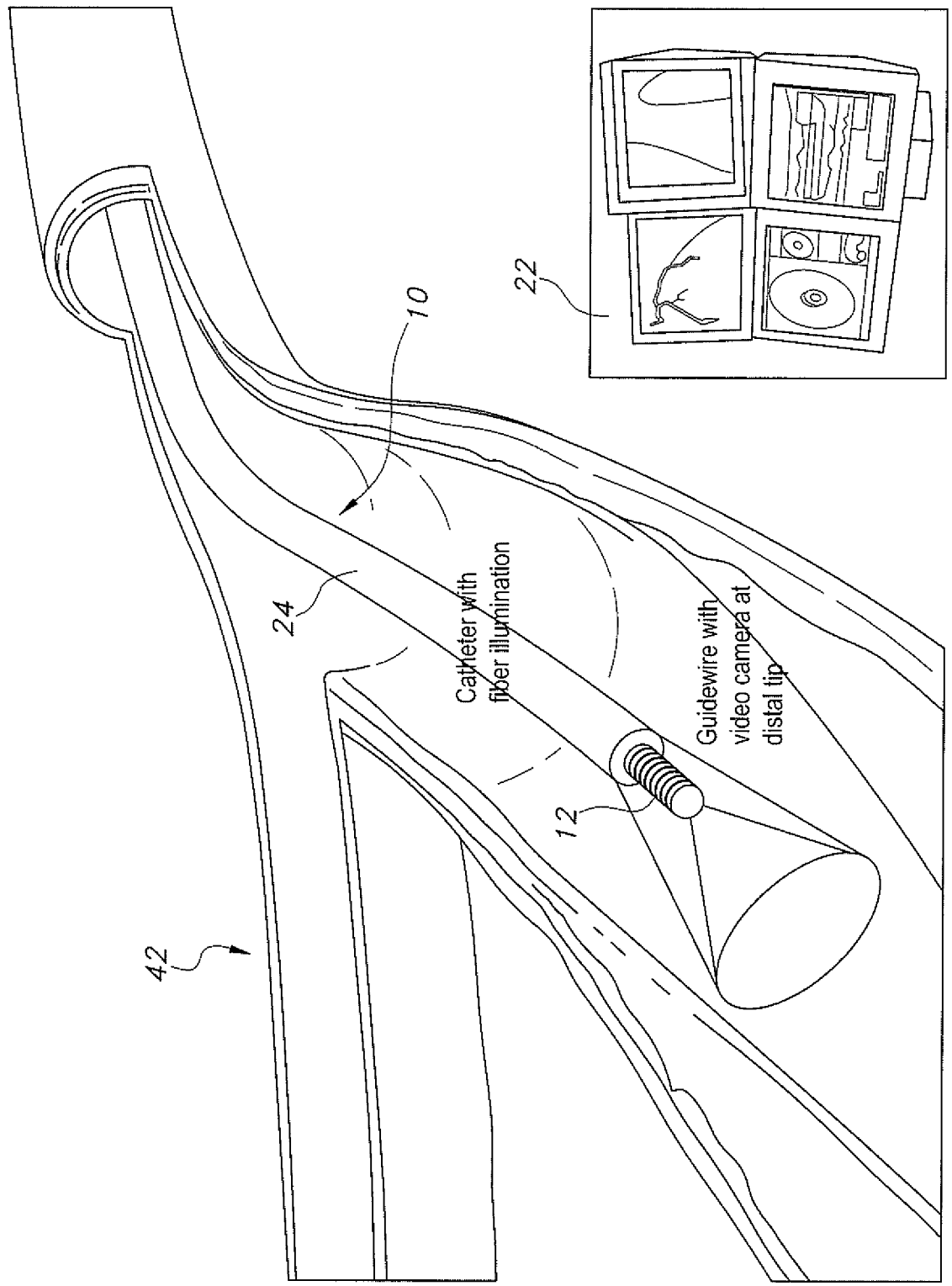
FIG. 1 is a schematic view of an exemplary guidewire and catheter system 10 according to the present invention moving through the vasculature 42 of a patient; a visual display of the vasculature is also shown.
Figure 2:
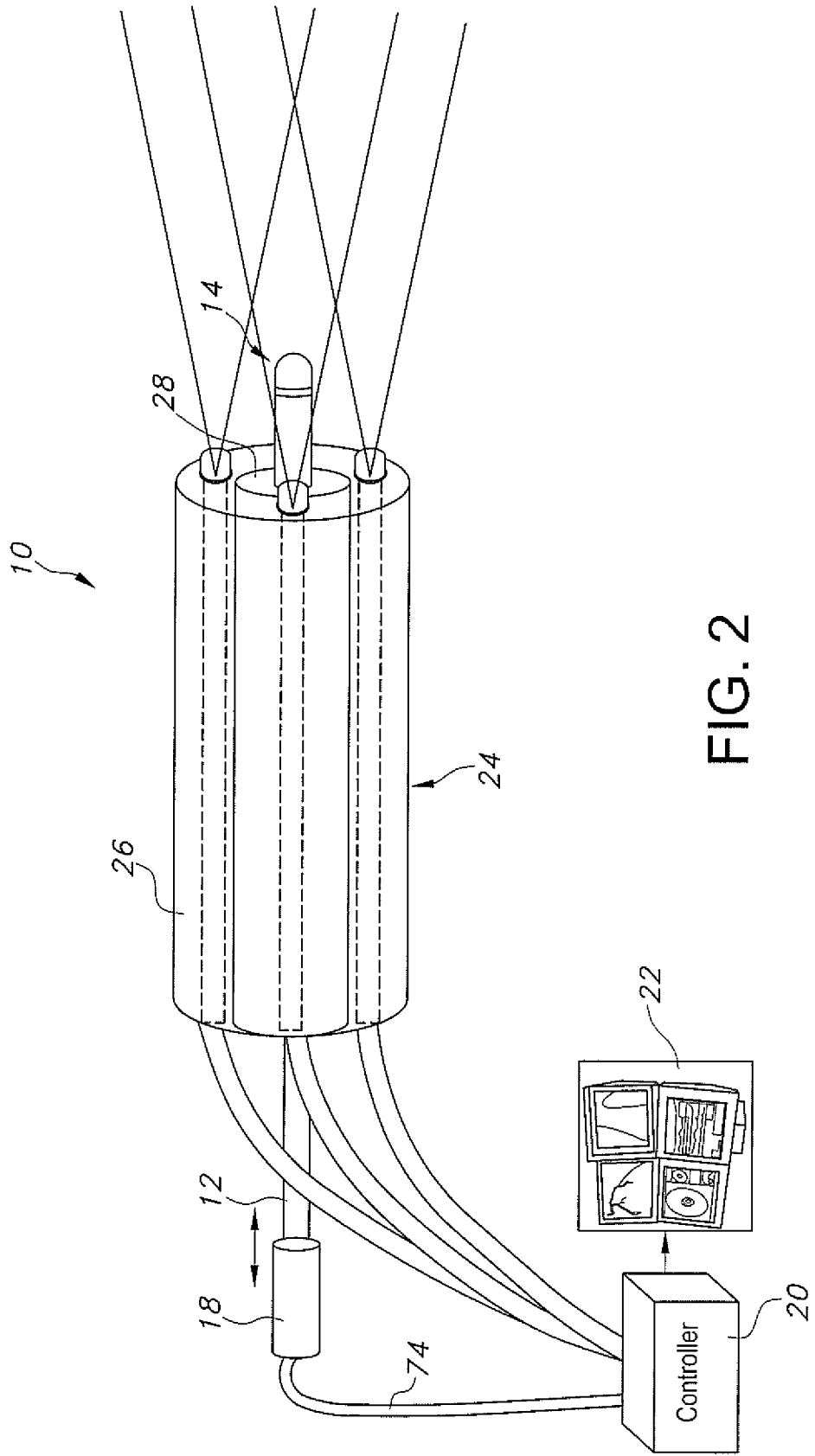
FIG. 2 is a side elevational view of the guidewire and catheter system 10 shown in FIG. 1.

Turning now to the drawings, an exemplary guidewire and catheter system 10 according to the present invention is generally illustrated in FIGS. 1 and 2. The system 10 comprises a guidewire 12 extending along a longitudinal axis A-A from a guidewire distal portion 12A (FIG. 3) to a proximal portion 12A (FIG. 4). The guidewire distal portion 12A has an atraumatic head 14 provided with a camera chip 16. The guidewire 12 is detachably connectable to a proximal connector 18 powered by a controller 20 that is wired to a visual display 22.

Separately, a catheter 24 of the system 10 has a cylindrically-shaped sidewall 26 that defines an axially-extending primary lumen 28. The catheter sidewall 26 supports a number of optical fibers, for example, optical fibers 30, 32 and 34. The optical fibers 30, 32 and 34 are evenly spaced at 120° intervals about the primary lumen 28 and extend through the sidewall 26 to respective light-emitting lenses 36, 38 and 40. The light-emitting lenses 36, 38 and 40 are configured to illuminate the vasculature 42 of a patient as the guidewire and catheter system 10 of the present invention is used in a medical procedure. The optical fibers 30, 32 and 34 are optically connected to the controller 20 to provide electrical power to the light-emitting lenses 36, 38 and 40.

In a preferred embodiment, each optical fiber 30, 32 and 34 in connected to a different wavelength spectrum coming from the controller 20 to allow multispectral illumination by the respective light-emitting lenses 36, 38 and 40 of a target tissue. Still images and video of the target tissue can thus be taken under white light and under multiple spectrums consecutively to give detailed information about the target tissue to the surgeon.

Referring to FIGS. 3 to 6, the guidewire 12 is shown in greater detail aligned along a longitudinal axis A-A and comprising a core wire 44 extending from a core wire proximal portion 44A having a proximal end 44B to a core wire distal portion 44C having a distal end 44D. A core wire intermediate portion 44E resides between the core wire proximal and distal portions 44A, 44C. A proximal tapered portion 44F extends downwardly and proximally along the longitudinal axis A-A from the intermediate portion 44E to the core wire proximal portion 44A. Similarly, a distal tapered portion 42G extends downwardly and distally along the longitudinal axis A-A to the core wire distal portion 44C. The atraumatic head assembly 14 supporting the camera chip 16 is connected to the core wire distal end 44D.

In an alternate embodiment, the core wire 44 is replaced with a hypotube.

Figure 3:
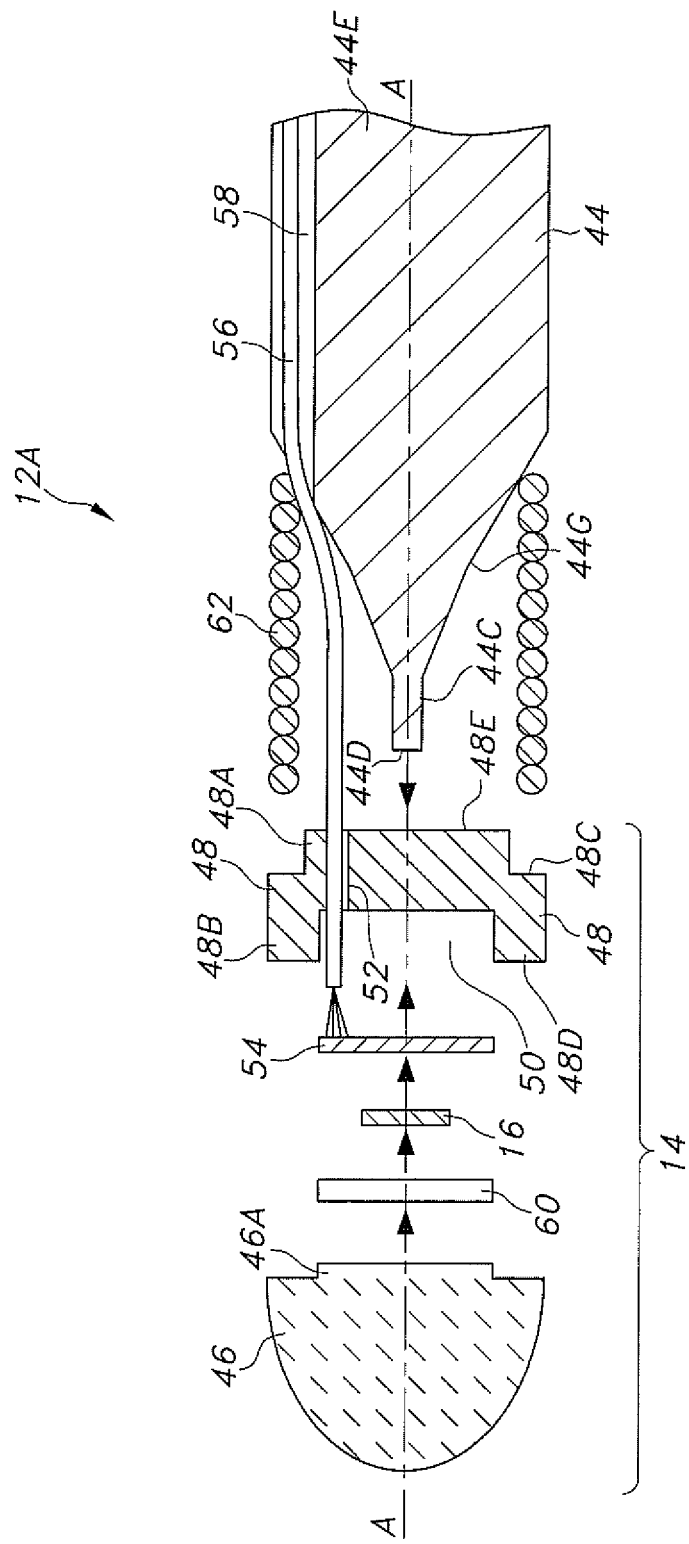
FIG. 3 is a cross-sectional and exploded view of a distal portion 12A of the guidewire 12 shown in FIG. 1.
Figure 4:
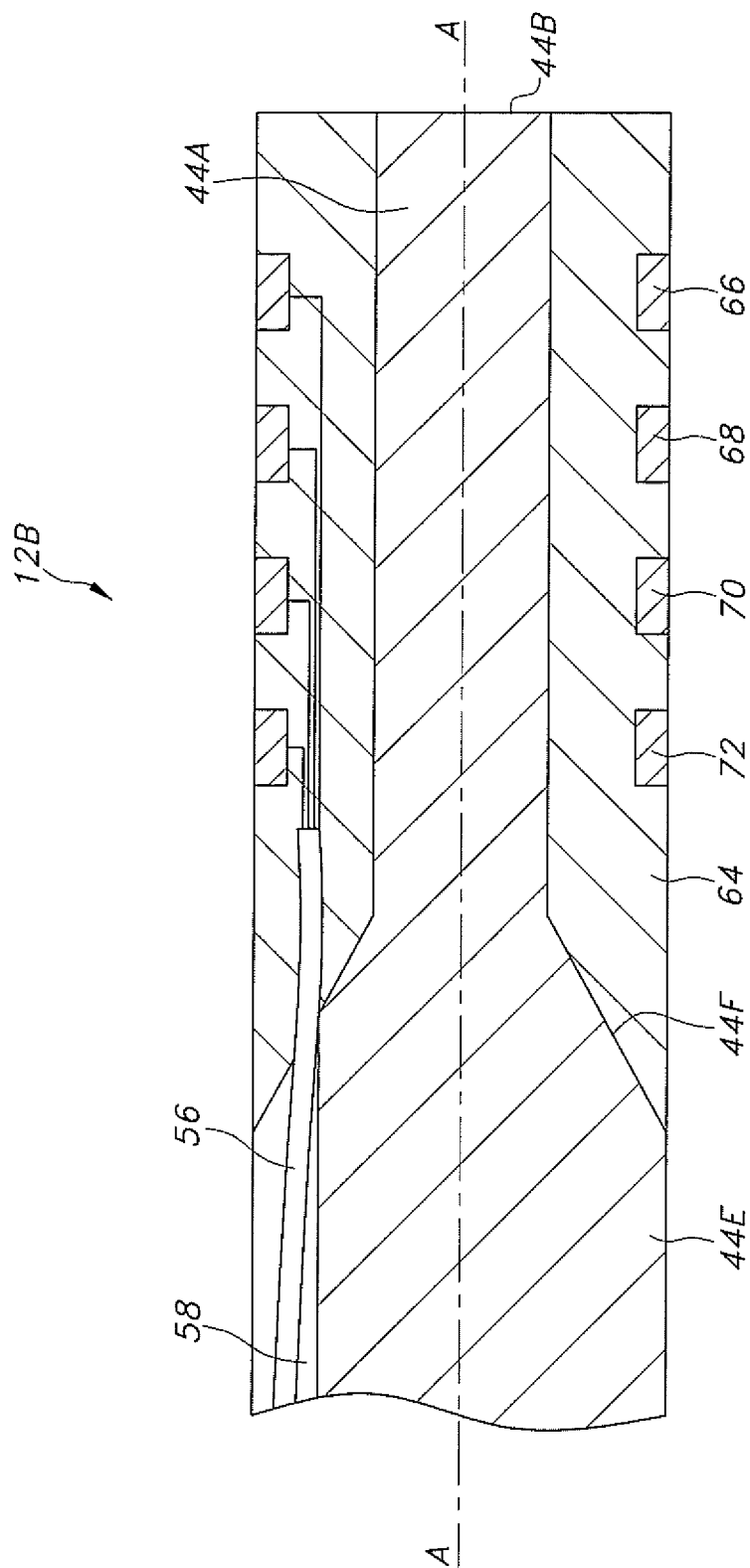
FIG. 4 is a cross-sectional view of a proximal portion 12B of the guidewire 12 shown in FIG. 1.

FIG. 3 illustrates the distal portion 12A of the guidewire 12 and the atraumatic head 14 in greater detail. The atraumatic head 14 comprises a plano-convex atraumatic lens 46 connected to a medical grade polymeric material or a metal housing 48. If metal, stainless steel is preferred for the housing. The housing 48 comprises a cylindrically-shaped proximal section 48A meeting an enlarged diameter cylindrically-shaped distal section 48B at an annular step 48C. The housing distal section 48B has an annular rim 48D that surrounds a recess 50.

The atraumatic lens 46 has a proximal section 46A of a reduced diameter that is sized and shaped to snuggly fit into the recess 50 of the housing 48. In that manner, the atraumatic lens is supported by the housing. The lens 46 preferably has a hemispherical- or parabolic-shaped exterior surface so that tissue trauma is minimized as the guidewire 12 moves through the vasculature of a patient. Suitable materials for the lens 46 include optical glasses such as silicon dioxide, fused silica and quartz, zinc selenide, zinc sulfide, germanium, sapphire, calcium fluoride, and barium fluoride. Optical plastics such as optical silicone elastomers, poly methyl methacrylate, polycarbonate, and polystyrene are also suitable materials for the lens 46.

An off-set bore 52 extends through the housing 48 from a proximal face 48E to the recess 50. A double-sided or multilayer printed circuit board (PCB) 54 is nested in the recess 50. The PCB 54 mechanically supports the camera chip 16, which is preferably a CMOS or CCD camera chip, and electrically connect the camera chip to the electrical cable 56. The PCB 54 has conductive tracks, pads and other electrical features (not shown) etched from one or more layers of copper laminated onto or between layers of a non-conductive substrate. The CMOS or CCD camera chip 16 is soldered onto or otherwise attached to the PCB 54 to mechanically fasten the two components together and electrically connect the camera chip to the electrical cable 56.

An electrical cable 56 extends along a groove 58 in the core wire 44, through the bore 52 in the housing 48 to the camera chip 16 supported on the PCB 54. The camera chip 16 is protected from damage during use by a transparent protective coating 60.

As shown in FIG. 3, prior to connecting the atraumatic head 14 to the distal end 44D of the core wire 44, a distal coil spring 62 is fitted over the distal portion 44C of the core wire. A proximal end of the coil spring 62 is connected to the distal tapered portion 44G of the core wire 44. At its opposed distal end, the coil spring 62 is connected to the housing 48 for the atraumatic head at the annular step 48C.

FIG. 4 is an enlarged view of the proximal portion 12B of the guidewire 12. This drawing shows the proximal tapered portion 44F of the core wire 44 residing between the core wire proximal and intermediate portions 44A, 44E. An electrically insulative polymeric sleeve 64 is supported on the core wire proximal portion 44A and the proximal taper 44F. The polymeric sleeve 64 supports a number of spaced-apart ring-shaped electrical contacts, for example, four electrical contacts 66, 68, 70 and 72. The electrical contacts 66, 68, 70 and 72 are individually connected to insulated electrical wires, which are bundled together to form the guidewire electrical cable 56 electrically connected to the PCB 54 in the housing 48 for the atraumatic head 14.

Figure 5:
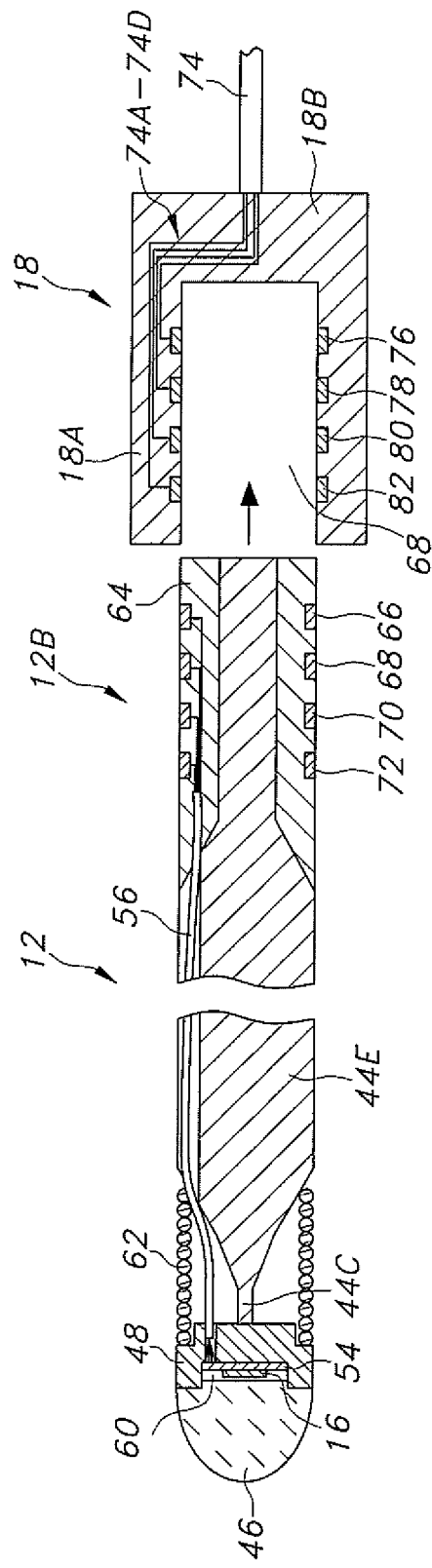
FIG. 5 is a cross-sectional view of the guidewire 12 being electrically connected to the proximal connector 18 shown in FIG. 1.
Figure 6:
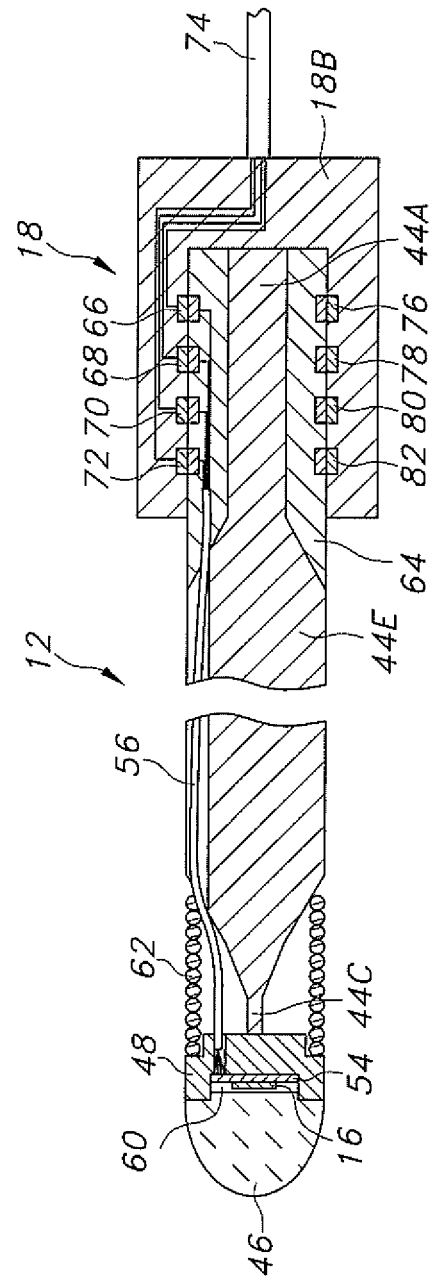
FIG. 6 is a cross-sectional view of the guidewire 12 and proximal connector 18 shown in FIG. 5 being electrically connected.

FIGS. 5 and 6 illustrate the proximal connector 18 comprising an open-ended housing of an electrically insulative material. The connector housing has an annular sidewall 18A surrounding a channel 68 leading to an end wall 18B. A primary electrical cable 74 connecting from the controller 20 (FIG. 1) leads to the end wall 18B where the cable splits into insulated electrical wires 74A, 74B, 74C and 74D. The connector sidewall 18A supports a number of spaced apart ring-shaped electrical contacts, for example, four electrical contacts 76, 78, 80 and 82. The insulated wires 74A to 74D are electrically connected to respective ones of the electrical contacts 76, 78, 80 and 82. The channel 68 in the proximal connector 18 is sized and shaped to receive the proximal portion 12B of the guidewire 12. With the proximal portion 12B housed inside the connector channel 68, the ring-shaped electrical contacts 76, 78, 80 and 82 of the proximal connector 18 are electrically connected to the ring-shaped electrical contacts 66, 68, 70 and 72 of the guidewire 12. Connecting the guidewire 12 to the proximal connector 18 thereby establishes electrical continuity from the controller 20 to the chip camera 16 supported on the PCB 54 in the atraumatic head 14.

Figure 7A:
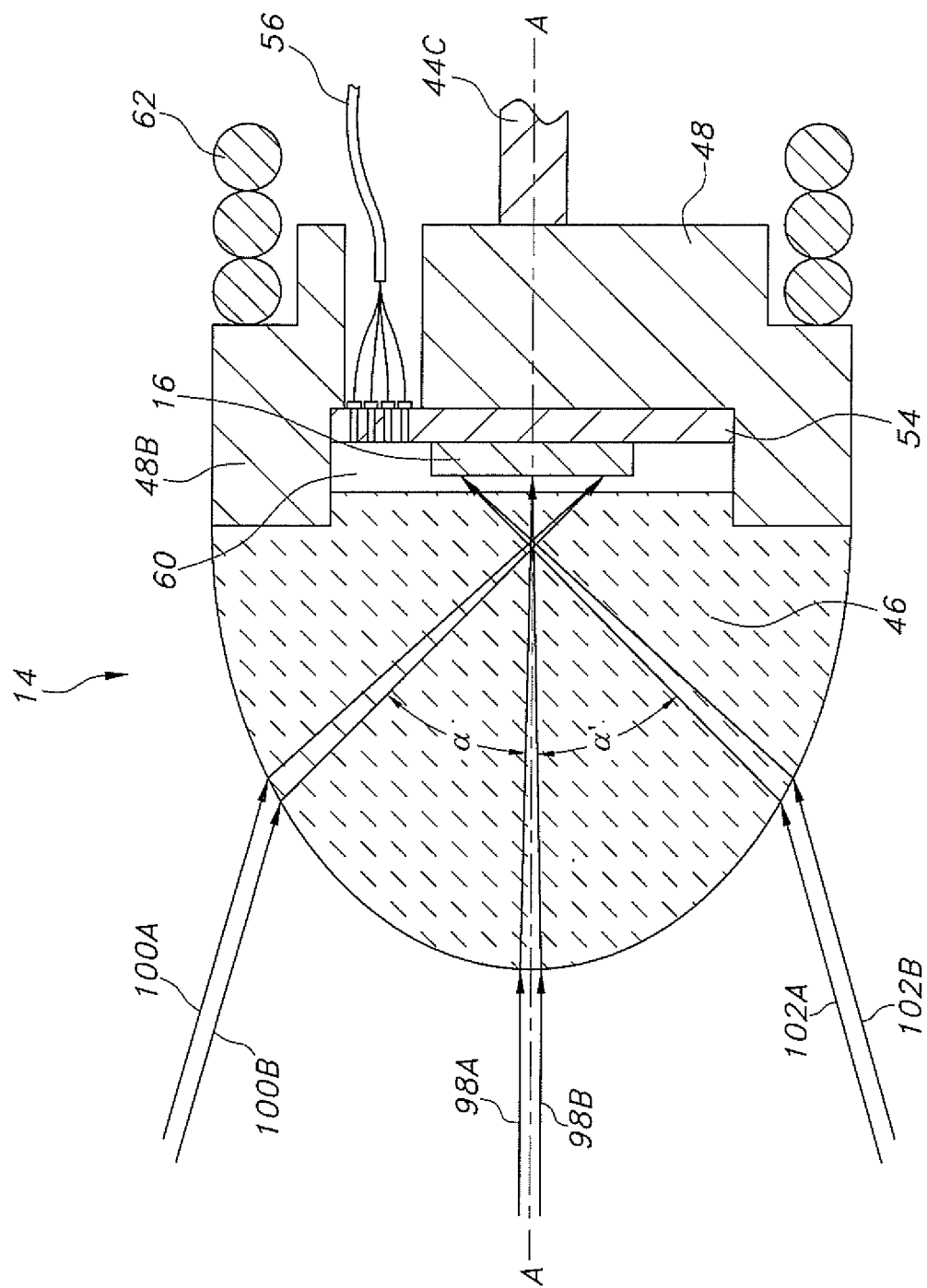
FIG. 7A is a cross-sectional view of the atraumatic head 14 for the guidewire 12 showing the paths of various incoming light rays as they travel through the lens 46 before impinging on the camera chip 16.

FIG. 7A shows one embodiment for the atraumatic head 14 of the guidewire 12 of the present system 10. In this drawing the light rays are shown emanating from a distant object (not shown) that is relatively far from the lens 46. In this situation, the light rays 98A and 98B are regarded as effectively parallel. This pair of light rays 98A and 98B travels axially along the longitudinal axis A-A through the atraumatic lens 46 and the protective coating 60 to then impinge on the camera chip 16 with minimal refraction from the longitudinal axis.

Another pair of light rays 100A and 100B emanating from the distant object at a distance that is significantly laterally above the axis of light rays 98A, 98B is shown impinging on the lens 46. The lens 46 causes these light rays 100A and 100B to refract inwardly at an angle alpha "α" across the longitudinal axis A-A inside the lens 46 to then impinge on the focal plane of the lens below the longitudinal axis where the camera chip 16 is positioned (the focal plane is aligned along the forward or distal face of the chip 16). Conversely, light rays 102A and 102B are shown impinging on the lens 46 from a distance that is substantially below the path of the axial light rays 98A, 98B. The lens 46 causes these light rays 102A, 102B to refract inwardly at an angle alpha "α'" across the longitudinal axis A-A inside the lens 46 to then impinge on the focal plane of the lens below that axis. An inverted image of the distant object results from the light ray pairs 98A, 98B and 100A, 100B and 102A and 102B impinging on the camera chip 16 positioned at the focal plane at different locations along its face.

Figure 7B:
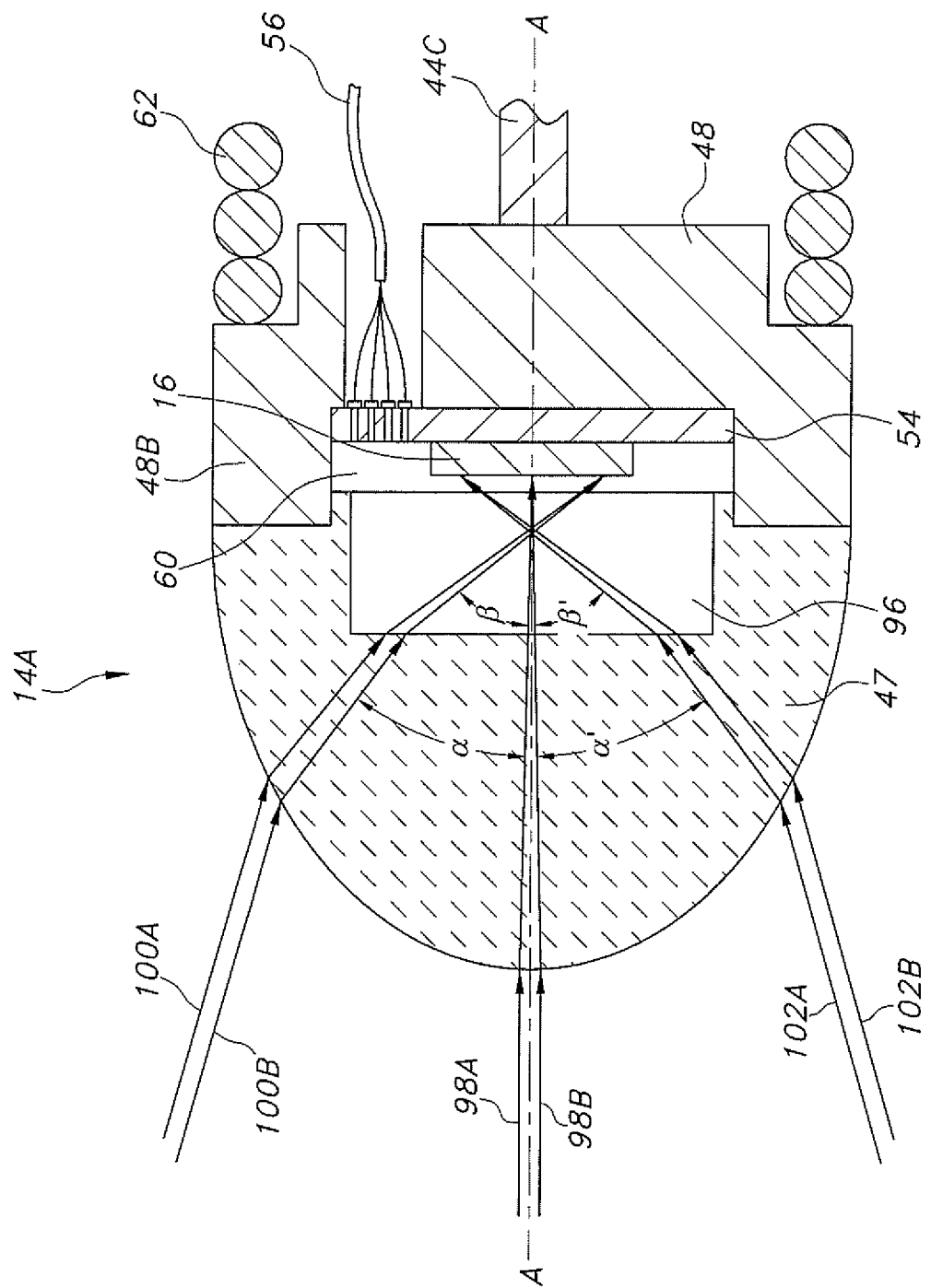
FIG. 7B is a cross-sectional view of an atraumatic head 14A for the guidewire 12 showing the paths of various incoming light rays as they travel through a lens 47 and then a disc-shaped void space 96 before impinging on the camera chip 16.

FIG. 7B shows another embodiment of an atraumatic head 14A according to the preset invention. The atraumatic head 14A has a lens 47, which has a hemispherical- or parabolic-shaped exterior surface and is made of similar materials as previously described for lens 46, that includes a disc-shaped void space 96 immediately adjacent to the transparent protective coating 60. The benefit of having the void space 96 is that it adds a second medium in addition to the atraumatic lens 47 through which light rays must pass before they impinge on the focal plane (the focal plane is aligned along the forward or distal face of the chip 16). That way, the void space 96 provides a degree of control over the position of the focal plane of the lens where the distal face of the camera chip 16 is positioned.

Looking first at light rays 98A and 98B, which are regarded as effectively parallel, they travel along the longitudinal axis A-A through the atraumatic lens 47, the void space 96 and the protective coating 60 with minimal refraction to then impinge on the focal plane of the lens where the distal face of the camera chip 16 is positioned.

The second pair of light rays 100A and 100B emanating from the distant object at a distance that is spaced significantly laterally above the axis of light rays 98A, 98B is shown impinging on the atraumatic lens 47, which causes these light rays 100A and 100B to refract inwardly toward the longitudinal axis A-A through the lens at a refraction angle alpha "α" before they enter the void space 96. Light rays 100A and 100B then refract a second time at a greater acute refraction angle beta "β" (α<β) with respect to the axis A-A through the disc-shaped void space 96 where they cross the longitudinal axis A-A inside the void space to pass through the protective coating 60 before impinging on the focal plane of the lens where the distal face of the camera chip 16 is positioned and below the longitudinal axis.

Conversely, light rays 102A and 102B are shown impinging on the lens 47 from a distance that is spaced substantially below the axial path of light rays 98A, 98B. The lens 47 causes these light rays 102A, 102B to refract inwardly toward the longitudinal axis A-A through the lens at a refraction angle alpha "α'" before entering the void space 96 where they refract a second time at a greater acute refraction angle beta "β'" (α'<β') with respect to the axis A-A. In the disc-shaped void space 96, the light rays 102A, 102B cross the longitudinal axis A-A to then pass through the protective coating 60 before impinging on the focal plane of the lens below the longitudinal axis. The second refraction angles β and β' through the disc-shaped void space 96 are intended to cause a greater number of light rays that are incident the outer periphery of the atraumatic lens 47 to ultimately impinge on the the camera chip 16. An inverted image of the distant object results from the light rays 98A, 98B and 100A, 100B and 102A and 102B impinging on the camera chip 16 at different locations along its face.

Figure 7C:
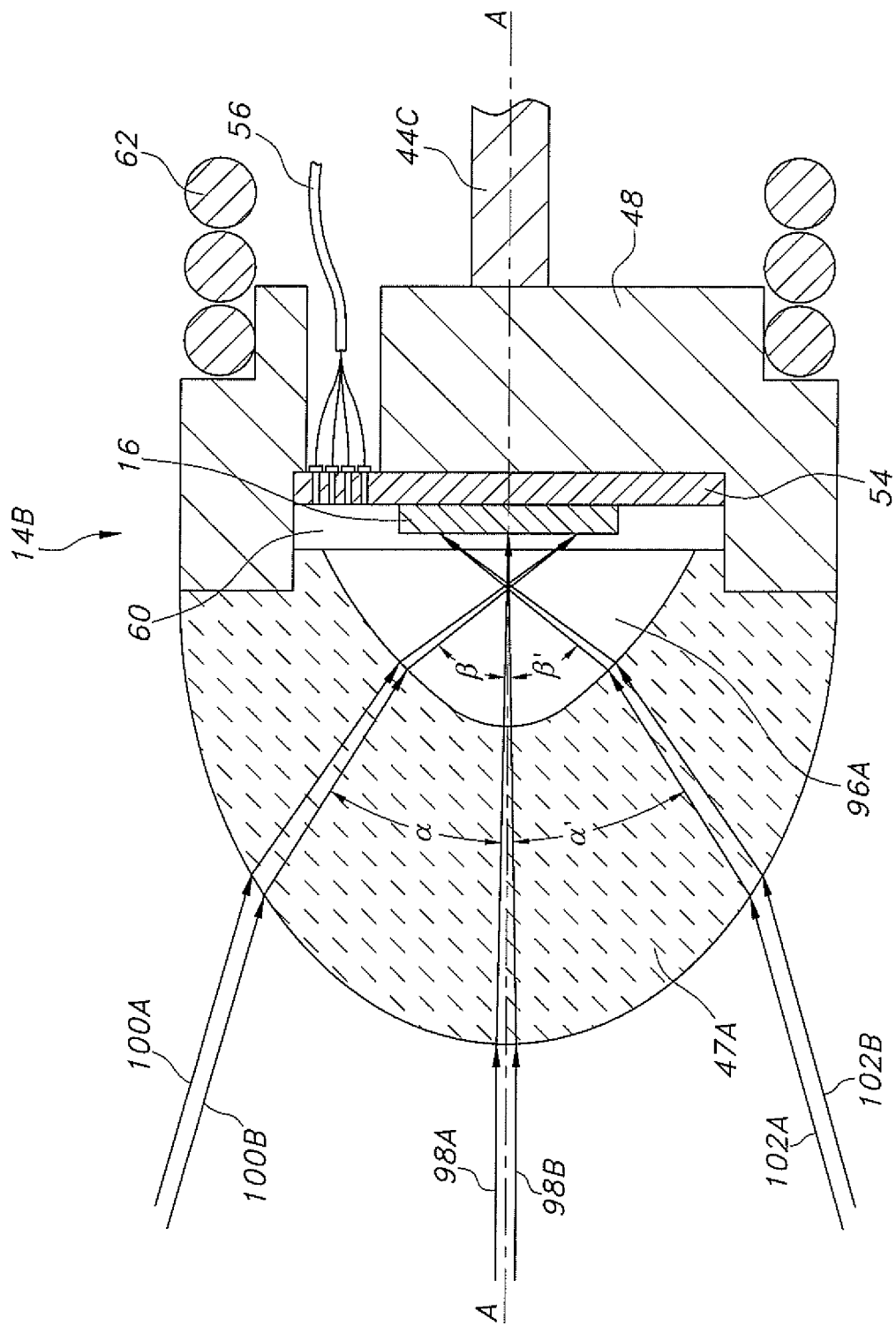
FIG. 7C is a cross-sectional view of an atraumatic head 14B for the guidewire 12 showing the paths of various incoming light rays as they travel through a lens 47A and then a hemispherical- or parabolic-shaped void space 96A before impinging on the camera chip 16.

FIG. 7C illustrates another embodiment of the atraumatic head 14B where the light rays emanate from a distant object (not shown) that is relatively far from the lens 47A. The lens 47A is similar to the atraumatic lens 47 shown in FIG. 7B, except that instead of a disc-shaped void space 96, there is a hemispherical- or parabolic-shaped void space 96A. As with the disc-shaped void space 96 shown in FIG. 7B, the hemispherical- or parabolic-shaped void space 96A adds a second medium in addition to the atraumatic lens 47A through which the light rays 98A, 98B, 100A, 100B, 102A and 102B must refract before they impinge on the camera chip 16 (the forward or distal face of the chip 16 is aligned along the focal plane).

Light rays 98A and 98B are regarded as effectively parallel and travel along the longitudinal axis A-A through the atraumatic lens 47A, the void space 96A and the protective coating 60 to then impinge on the camera chip 16 at the focal plane of the lens with minimal refraction.

The second pair of light rays 100A and 100B emanating from the distant object at a distance that is spaced significantly laterally above the axis of light rays 98A, 98B is shown impinging on the atraumatic lens 47A which causes these light rays 100A and 100B to refract inwardly toward the longitudinal axis A-A through the lens at a refraction angle alpha "α" before entering the hemispherical- or parabolic-shaped void space 96A. Light rays 100A and 100B then refract a second time at a greater acute refraction angle beta "β" (α<β) with respect to the axis A-A through the hemispherical- or parabolic-shaped void space 96A where they cross the longitudinal axis A-A to pass through the protective coating 60 before impinging on the focal plane of the lens 16 below the longitudinal axis.

FIG. 7C further shows light rays 102A and 102B impinging on the lens 47A from a distance that is spaced substantially below the axial path of light rays 98A, 98B. The lens 47A causes these light rays 102A, 102B to refract inwardly toward the longitudinal axis A-A through the lens at a refraction angle alpha "α'" before they enter the hemispherical- or parabolic-shaped void space 96A where they refract a second time at a greater acute refraction angle beta "β'" (α'<β') with respect to the axis A-A. In the hemispherical- or parabolic-shaped void space 96A, the light rays 102A, 102B cross the longitudinal axis A-A to then pass through the protective coating 60 before impinging on the focal plane of lens 16 below the longitudinal axis (the forward or distal face of the chip 16 is aligned along the focal plane). The second refraction angles β and β' through the hemispherical- or parabolic-shaped void space 96A are intended to cause a greater number of light rays that are incident the outer periphery of the hemispherical- or parabolic-shaped atraumatic lens 47A to ultimately impinge on the camera chip 16. An inverted image of the distant object results from the light rays 98A, 98B and 100A, 100B and 102A and 102B impinging on the focal plane of the lens and the camera chip 16 at different locations along the face of the camera chip.

Figure 8:
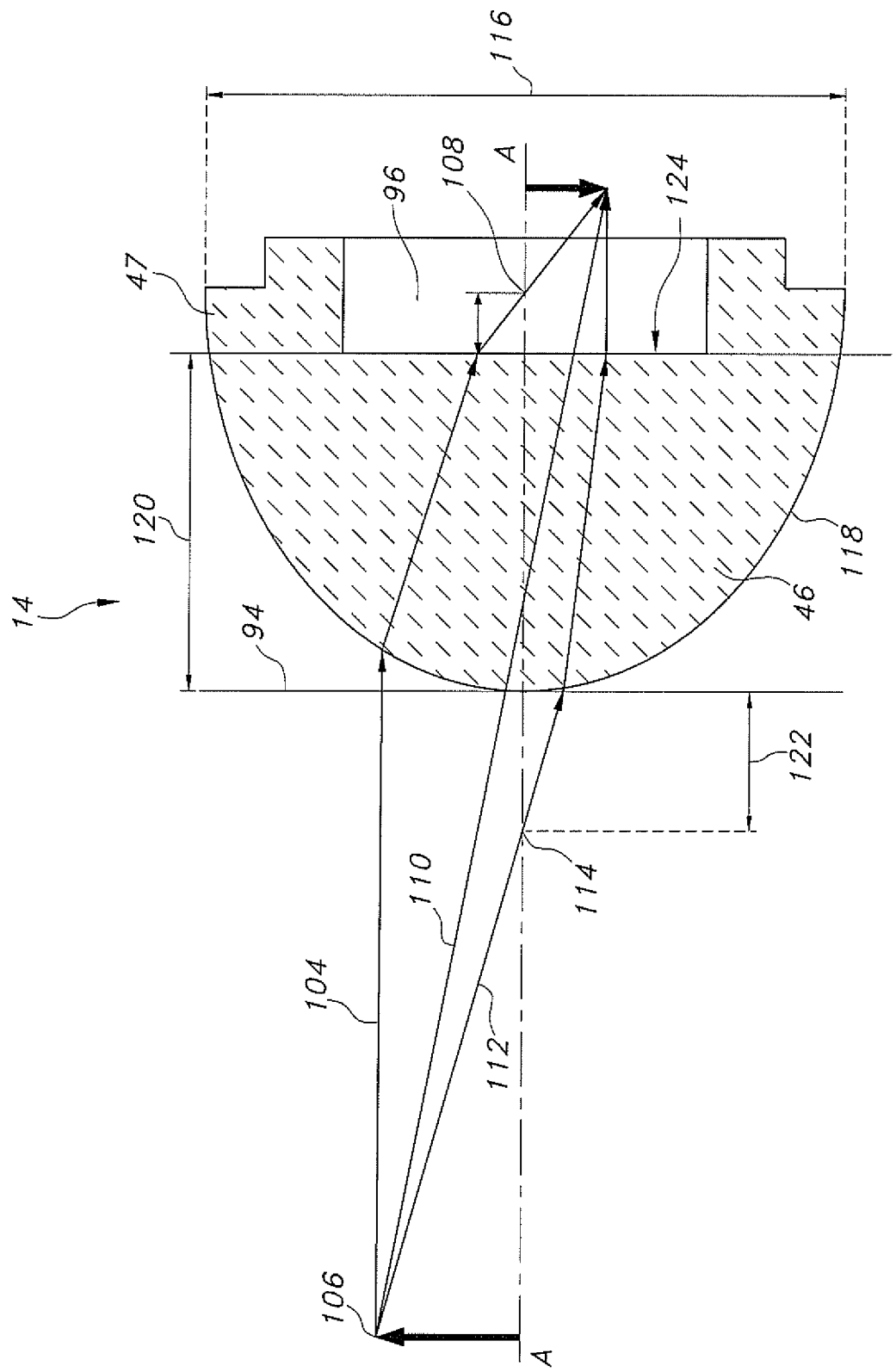
FIG. 8 is a cross-sectional view showing how an image of a target object/tissue is projected onto a camera chip 16 through the lens 46 shown in FIG. 7B.

FIG. 8 shows how an image of the target object/tissue is projected onto the camera chip 16 by geometrical ray tracing. A first ray 104 from the tip of the object 106 is aligned parallel to the longitudinal axis A-A passing through the lens 47 shown in FIG. 7B and then through a proximal focal point 108 in the disc-shaped void space 96. A second ray 110 is shown going from the tip of the object 106 directly through the lens 47 and disc-shaped void space 96 without any refraction. A third ray 112 from the tip of the object 106 is shown passing through a distal focal point 114 and then through the lens 47 where it refracts into the disc-shaped void space 96 aligned parallel to the longitudinal axis A-A. In an exemplary guidewire 12 having a diameter of about 0.014" (360 μm), the lens 47 has a diameter 116 of about 360 μm. If the lens has a radius of curvature 118 of 180 μm and a lens centre thickness 120 of 120 μm, then the distal focal length 122 is 390 μm from the tangent plane 94 and the proximal focal point 108 is 270 μm from a proximal surface 124 of the lens.

Figure 9:
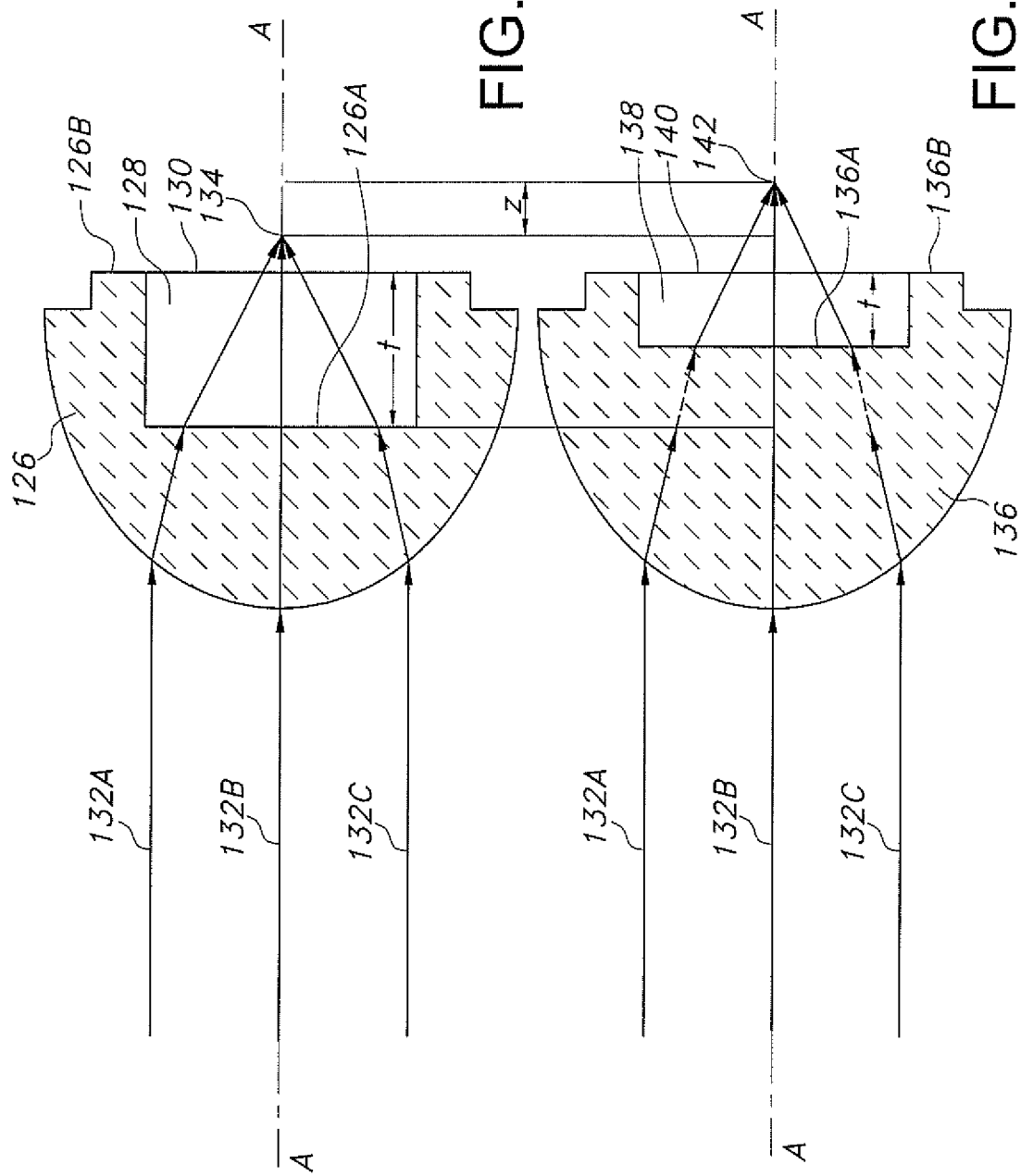
FIGS. 9A and 9B are cross-sectional views illustrating that as the thickness of the void space 96 in the lens 47 shown in FIG. 7B changes, that in turn changes the position of a respective proximal focal point 134 and 142.

Continuing from FIG. 7A where the atraumatic lens 46 does not have a void space in comparison to FIG. 7B where the atraumatic lens 47 has the disc-shaped void space 96, FIGS. 9A and 9B illustrate that as the thickness of the void space changes, the thickness of the lens changes which in turn changes the position of the proximal focal point. In FIG. 9A, the lens 126, which has a hemispherical- or parabolic-shaped exterior surface and is made of similar materials as previously described for lens 46, has a disc-shaped void space 128 with a thickness (t) aligned along the longitudinal axis A-A as measured from surface 126A to a plane 130 aligned along the proximal edge 126B of the lens. This lens 126 refracts light rays 132A, 132B and 132C to a focal point 134.

In contrast, FIG. 9B illustrates an atraumatic lens 136 where the disc-shaped void space 138 has a thickness (t') measure from surface 136A to a plane 140 aligned along the proximal edge 136B of the lens. This lens, which has a hemispherical- or parabolic-shaped exterior surface and is made of similar materials as previously described for lens 46, refracts light rays 132A, 132B and 132C to a focal point 142. With the thickness t of the void space 128 of lens 126 being greater than the thickness t' of the void space 138 of lens 136 (t>t'), it is shown that the focal point 142 of lens 136 has shifted proximally along the longitudinal axis A-A in comparison to the focal point 134 of lens 126 by distance (z).

Thus, as the lens thickness increases or the thickness of the disc-shaped void space decreases, the light rays 132A, 132B and 132C from a distant image are displaced further from a plane aligned along the proximal edge of the lens. The image is displaced by an amount $\Delta z = N-1/N$, where N is the refractive index of the lens (assuming the disc-shaped void space is filled with air). The hemispherical- or parabolic-shaped void space 96A of lens 47A shown in FIG. 7C will displace the focal point in a similar manner.

Figure 10:
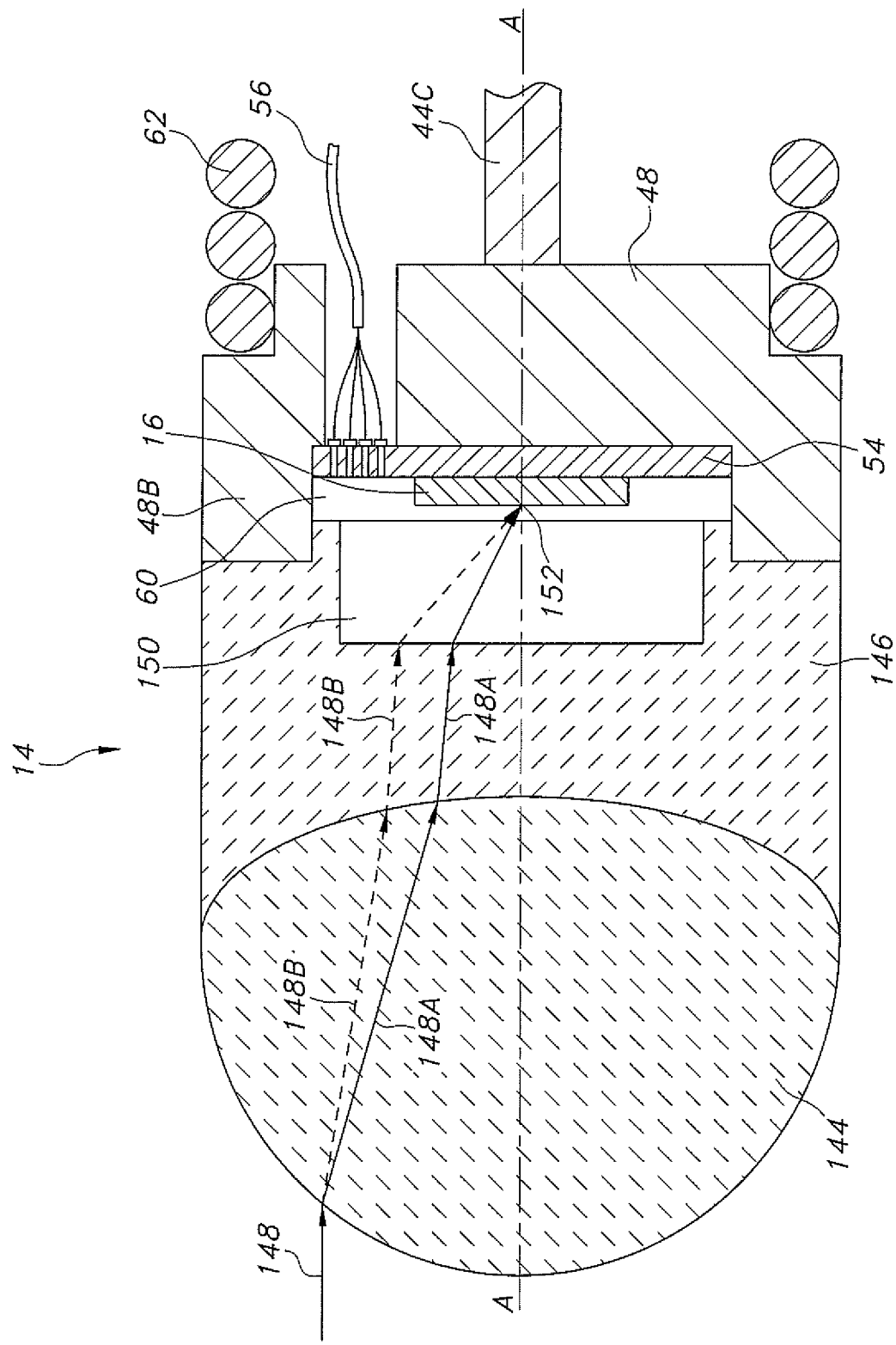
FIG. 10 is a cross-sectional view of another embodiment of an atraumatic head 14C having an achromatic lens doublet comprising a distal lens 144 optically connected to a proximal lens 146 to limit the effects of chromatic and spherical aberration.

FIG. 10 illustrates another embodiment of an atraumatic head 14C according to the present invention. The atraumatic head 14C has an achromatic lens doublet that limits the effects of chromatic and spherical aberration and comprises a distal lens 144 optically connected to a proximal lens 146. The distal and proximal lens 144, 146 are individually made from glasses with different amounts of dispersion. The distal lens 144 is a negative (concave) lens made from flint glass such as F2, which has a relatively high dispersion that splits an incoming light ray 148 into its component wavelengths 148A and 148B. The proximal lens 146 is a positive (convex) lens made from crown glass such as BK7, which has a relatively lower dispersion. The chromatic aberration of the distal lens 144 is essentially counterbalanced by that of the proximal lens 146. The proximal lens 146 permits the component wavelengths 148A and 148B to enter the disc-shaped void space 150 where they are refracted to a common focal point 152 on the focal plane of the combined lens system where the camera chip 16 is positioned (the focal plane is aligned along the forward or distal face of the chip 16).

Figure 11:
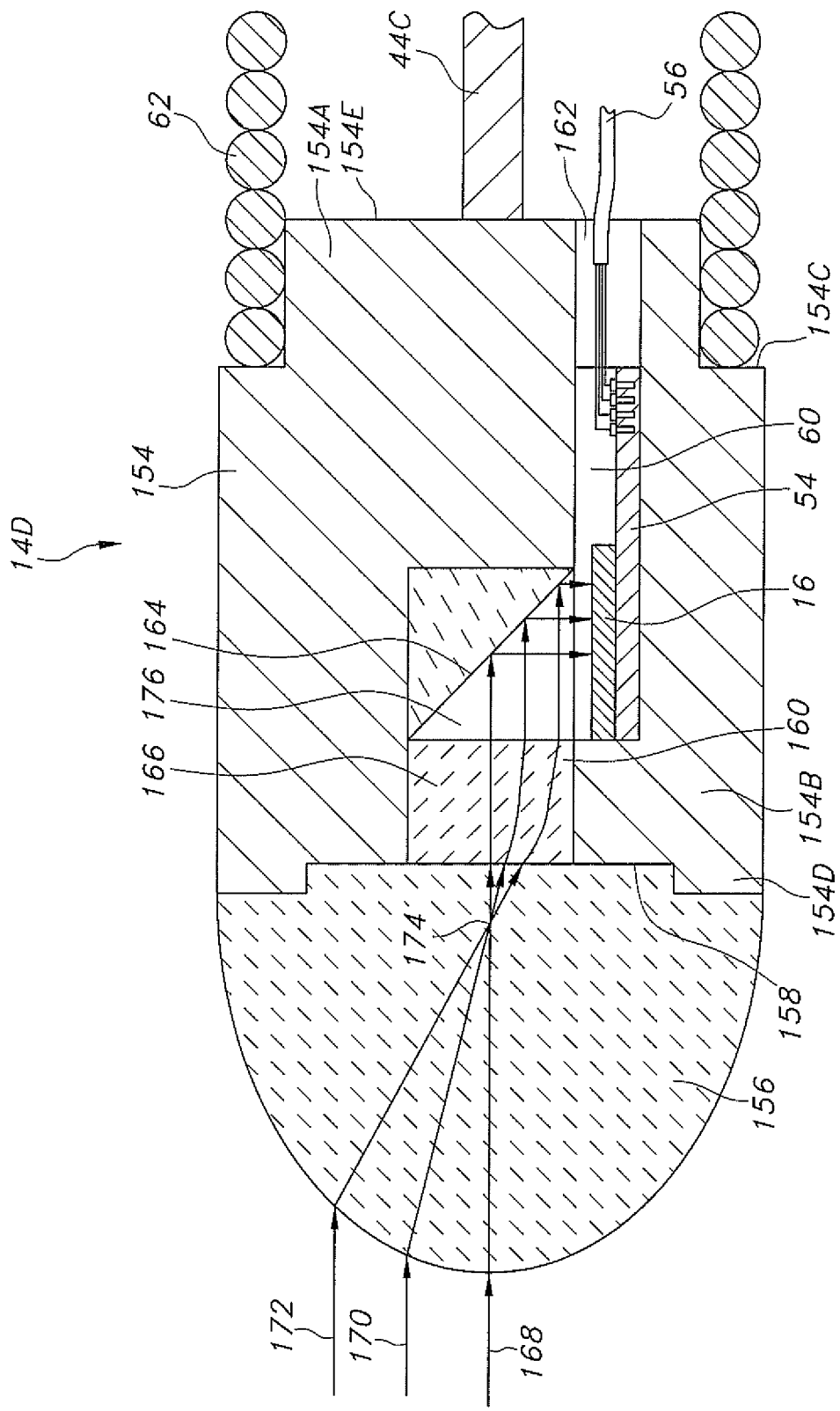
FIG. 11 is a cross-sectional view of another embodiment of an atraumatic head 14D showing light rays entering an atraumatic lens 156 optically coupled to a collimating GRIN lens 166 before reflecting off a mirror 164 to then impinge on a camera chip 16.

FIG. 11 illustrates another embodiment of an atraumatic head 14D according to the present invention. The atraumatic head 14D has a housing 154 supporting an atraumatic lens 156. Lens 156 has a hemispherical- or parabolic-shaped exterior surface and is made of similar materials as previously described for lens 46. The housing comprises a cylindrically-shaped proximal section 154A meeting an enlarged diameter cylindrically-shaped distal section 154B at an annular step 154C. The housing distal section 154B has an annular rim 154D that surrounds a recess 158 leading to an inlet 160. A reduced diameter proximal portion of the atraumatic lens 156 is fitted into the recess 158 leading to the inlet 160 of the housing 154.

An off-set bore 162 extends through the housing 154 from a proximal face 154E to the inlet 160. A printed circuit board (PCB) 54 resides in the inlet 158 to mechanically support the camera chip 16, which is preferably a CMOS or CCD camera chip. The CMOS or CCD camera chip 16 is soldered onto or otherwise attached to the PCB 54 to mechanically fasten the two components together and electrically connect the camera chip to the electrical cable 56.

The electrical cable 56 extending along the groove 58 in the core wire 44 (FIGS. 3 and 4) electrically connects to the PCB 54 in the bore 162. The camera chip 16 is protected from damage by the transparent protective coating 60. A prism-shaped mirror 164 is fitted into a proximal portion of the inlet 160. Then, a collimated gradient-index (GRIN) lens 166 having a parabolic variation of refractive index with radial distance from the longitudinal axis A-A (radial gradient of refractive index) is seated in a distal portion of the inlet 160 abutting an edge of the prism-shaped mirror 162. The mirror 164 is angles at 45° to the plane of the collimated image of the GRIN lens 166. The distal atraumatic lens 156 is made of a glass that causes exemplary incoming light rays 168, 170 and 172 to refract to a focal point 174 inside the lens 156. This point is the distal focal point of the GRIN lens 166. The light rays 168, 170 and 172 disperse past the focal point 174 as they enter the GRIN lens 166.

Light ray 168 is shown entering the distal lens 156 along the longitudinal axis A-A. This light ray 168 travels along that axis through the atraumatic lens 156, the GRIN lens 166 and a proximal void space 176 before impinging on the mirror 164 which refracts the light ray 90° onto the camera chip 16.

Light ray 172 enters the atraumatic lens 156 spaced laterally above the longitudinal axis A-A to then refract through the focal point 176 before entering the GRIN lens 166 where it bends through the radial refractive index of that lens to then enter the proximal void space 176 aligned substantially parallel to but spaced from light ray 168 traveling along the longitudinal axis A-A. Light ray 172 then impinges on the mirror 164 to reflect 90° onto the camera chip 16.

Light ray 170 is shown entering the atraumatic lens 156 spaced from the longitudinal axis A-A and aligned between light rays 168 and 172. The atraumatic lens 156 refracts this light ray 170 through the focal point 176 before it enters the GRIN lens 166 where the light ray bends through the gradient of refractive index of that lens to then enter the proximal void space 176 aligned substantially parallel to, but between light rays 168 and 172. Light ray 170 then impinges on the mirror 164 where it is reflected 90° onto the camera chip 16.

Figure 12:
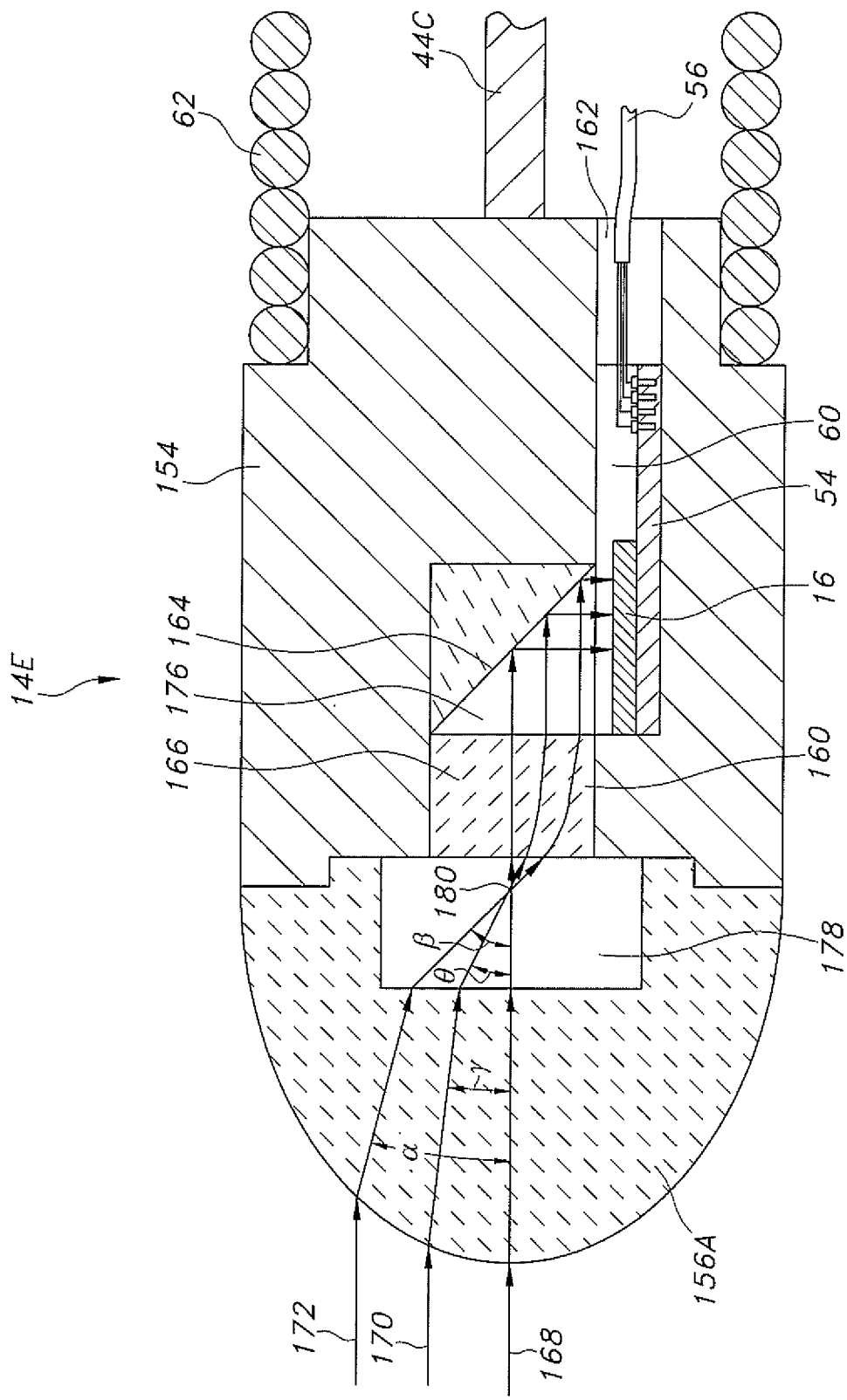
FIG. 12 is a cross-sectional view of another embodiment of an atraumatic head 14E that is similar to the atraumatic head 14D shown in FIG. 11, but with the atraumatic lens 156A having a disc-shaped void space 178.

FIG. 12 illustrates another embodiment of an atraumatic head 14E according to the present invention. The atraumatic head 14D has a housing 154 supporting an atraumatic lens 156A. Lens 156A has a hemispherical- or parabolic-shaped exterior surface and is made of similar materials as previously described for lens 156. Further, the housing for the atraumatic head 14E is substantially the same as the housing 154 for the atraumatic head 14D shown in FIG. 11. However, the atraumatic lens 156A has a distal disc-shaped void space 178 so that exemplary incoming light rays 168, 170 and 172 refract a first amount in the lens and then a second, greater amount in the distal void space to converge at a focal point 180 inside the void space 178. This point 180 is the distal focal point of the GRIN lens 166. The light rays 168, 170 and 172 then disperse past the focal point 180 as they travel further through the distal void space 178, the GRIN lens 166 and the proximal void space 176 before being reflected onto the camera chip by prism 164.

Light ray 168 is shown entering the distal lens 156A along the longitudinal axis A-A. This light ray 168 travels along that axis through the atraumatic lens 156A, the distal void space 178, the GRIN lens 166 and the proximal void space 176 before impinging on the mirror 164 which reflects the light ray 90° onto the camera chip 16.

Light ray 172 enters the atraumatic lens 156 spaced laterally above the longitudinal axis A-A to then refract through the focal point 176 before entering the GRIN lens 166 where it bends through the radial refractive index of that lens to then enter the proximal void space 176 aligned substantially parallel to but spaced from light ray 168 traveling along the longitudinal axis A-A. Light ray 172 then impinges on the mirror 164 to reflect 90° onto the camera chip 16.

Light ray 170 is shown entering the atraumatic lens 156 spaced from the longitudinal axis A-A and aligned between light rays 168 and 172. The atraumatic lens 156 refracts this light ray 170 through the focal point 176 before it enters the GRIN lens 166 where the light ray bends through the gradient of refractive index of that lens to then enter the proximal void space 176 aligned substantially parallel to, but between light rays 168 and 172. Light ray 170 then impinges on the mirror 164 where it is reflected 90° onto the camera chip 16.

It is worth noting that according to Snell's Law, the angle of refraction $\alpha$ for light ray 172 is greater than the angle of refraction $\gamma$ for light ray 170 in the atraumatic lens 156A. Similarly, the angle of refraction $\beta$ of light ray 172 is greater than the angle of refraction $\theta$ of light ray 170 in the distal disc-shaped void space 178. Snell's law is a formula that is used to describe the relationship between the angles of incidence and refraction, when referring to light or other waves passing through a boundary between two different isotropic media, such as water, glass, or air. In optics, the law is used in ray tracing to compute the angles of incidence or refraction, and in experimental optics to find the refractive index of a material. Snell's law states that the ratio of the sines of the angles of incidence and refraction is equivalent to the ratio of phase velocities in the two media, or equivalent to the reciprocal of the ratio of the indices of refraction.

Figure 13:
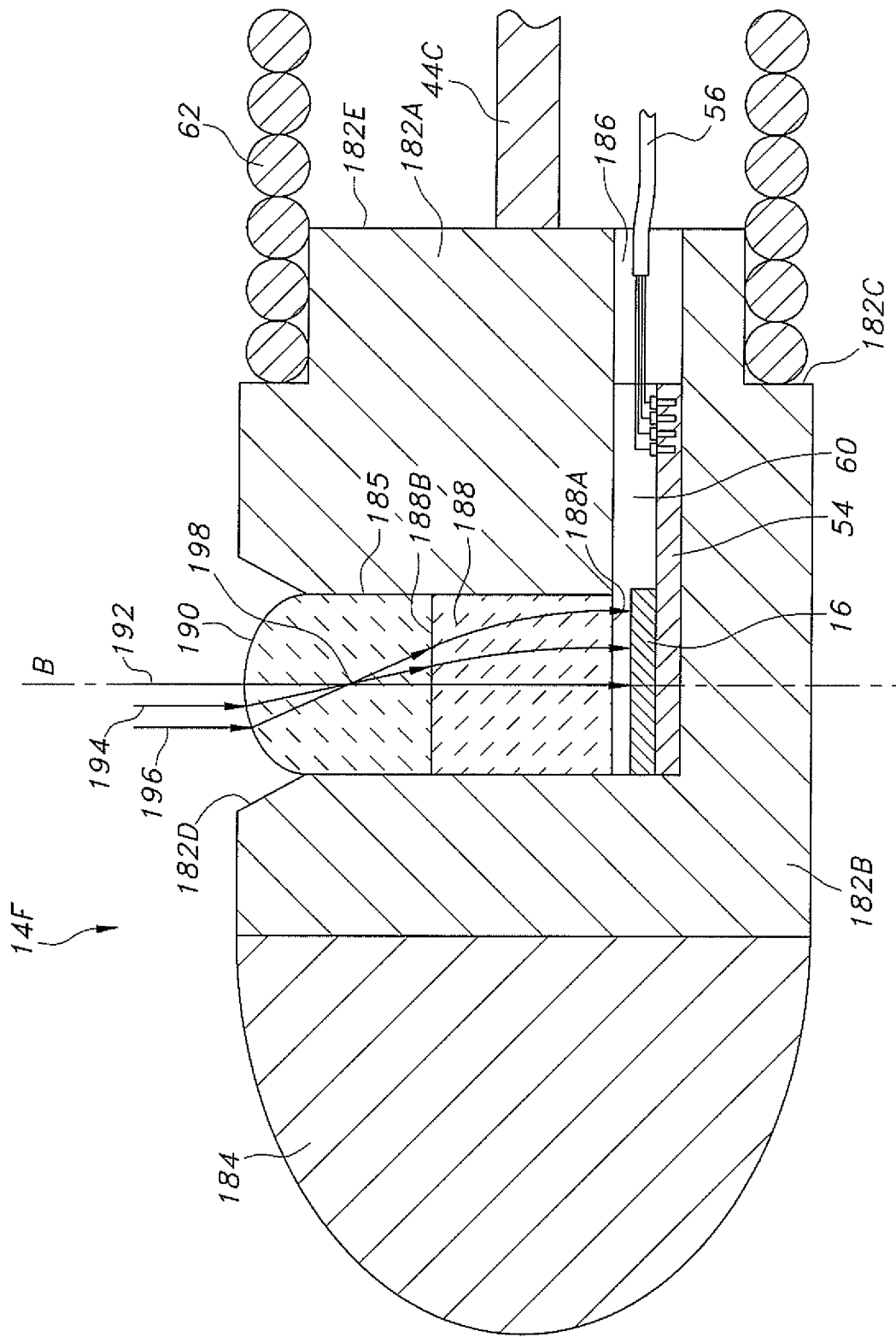
FIG. 13 is a cross-sectional view of another embodiment of an atraumatic head 14F showing light rays impinging on a lateral atraumatic lens 190 optically connected to a lateral collimating GRIN lens 188 with the light rays then being directed to the camera chip 16.

FIG. 13 illustrates an alternate embodiment of an atraumatic head 14F for the guidewire 10 shown in FIG. 1. This atraumatic head 14F comprises a housing 182 connected to the distal portion 44C of the core wire 44. The housing 182 supports a distal atraumatic tip 184 that is not a lens but has a hemispherical- or parabolic-shaped exterior surface that helps prevent tissue damage as the guidewire 10 is advanced through the vasculature 42 of a patient.

The housing 182 comprises a cylindrically-shaped proximal portion 182A meeting an enlarged diameter cylindrically-shaped distal portion 182B at an annular step 182C. An annular tapered sidewall 182D leads to a lateral inlet 185 which extends into the distal portion 182B of the housing where the inlet meets an off-set bore 186. The off-set bore 186 leads to a proximal face 182E of the housing. The printed circuit board (PCB) 54 resides in the off-set bore 186 to mechanically support the camera chip 16, which is preferably a CMOS or CCD camera chip, and electrically connect the camera chip to the electrical cable 56. A transparent coating 60 protects the camera chip 16 from damage.

A GRIN lens 188 resides in the lateral inlet 185 with its inner face 188A aligned with the off-set bore 186. An outer face 188B of the GRIN lens 188 supports a lateral atraumatic lens 190 which resides in the annular taper 182D. The lateral atraumatic lens 190 is made of a glass that causes exemplary incoming light rays 192, 194 and 196 to refract to a focal point 198 inside the lateral lens 190. This point is the distal focal point of the GRIN lens 188. The light rays 192, 194 and 196 disperse past the focal point 198 as they enter the GRIN lens 188.

Light ray 192 is shown entering the lateral lens 190 along a longitudinal axis B-B. This light ray 192 travels along that axis through the atraumatic lens 190 and the GRIN lens 188 before impinging on the camera chip 16 (the focal plane is aligned along the forward or distal face of the chip 16).

Light ray 196 enters the atraumatic lens 190 spaced from the longitudinal axis B-B to then refract through the focal point 198 before entering the GRIN lens 188 where it bends through the radial refractive index of that lens to then align substantially parallel to but spaced from light ray 192 traveling along the longitudinal axis B-B. Light ray 196 then impinges on the camera chip 16.

Light ray 194 is shown entering the atraumatic lens 190 spaced from the longitudinal axis B-B and aligned between light rays 192 and 196. The lateral atraumatic lens 190 refracts this light ray 194 through the focal point 198 before it enters the GRIN lens 188 where the light ray bends through the gradient of refractive index of that lens to then align substantially parallel to, but between light rays 192 and 196. Light ray 194 then impinges on the camera chip 16.

Figure 14:
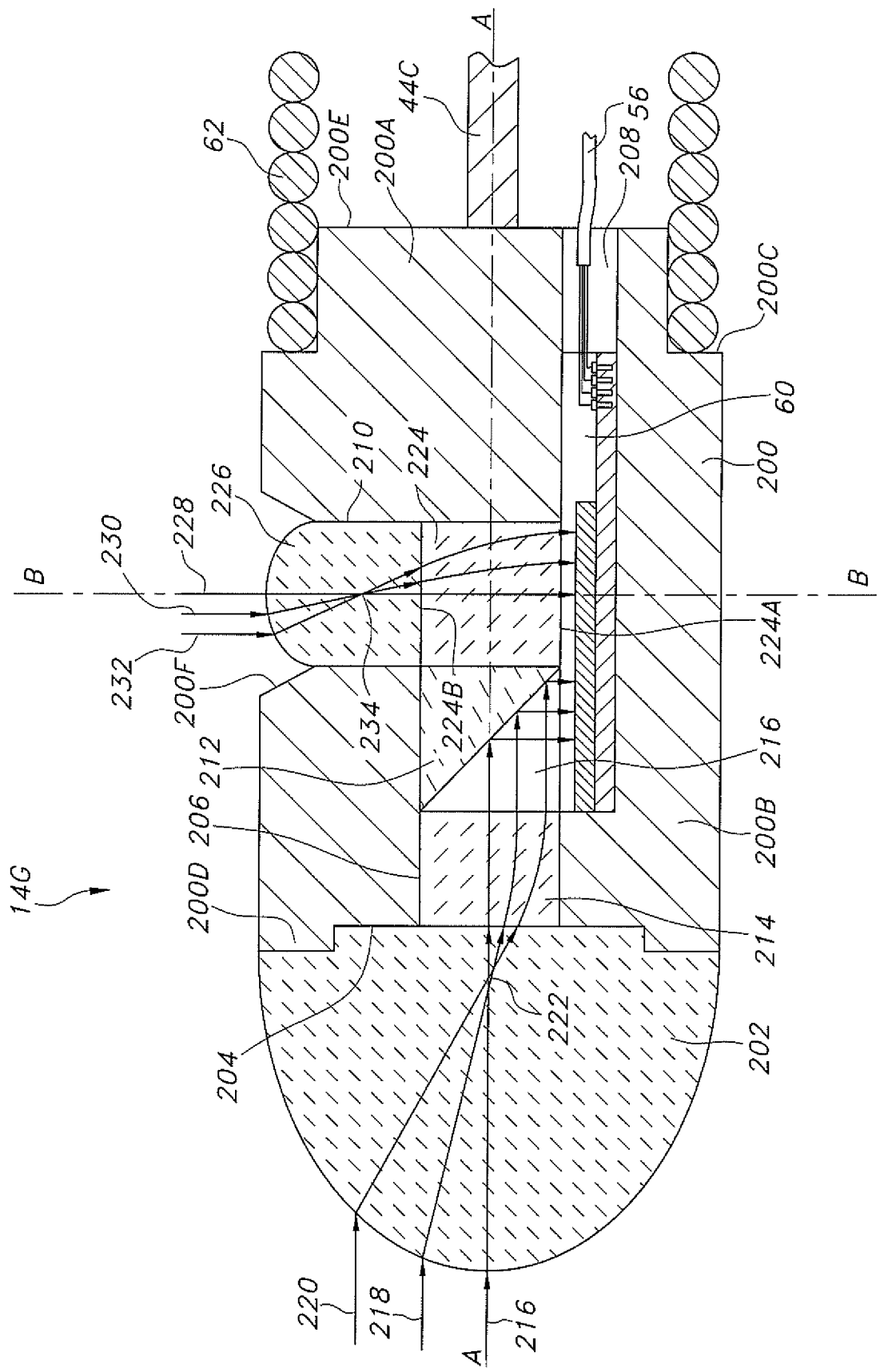
FIG. 14 is a cross-sectional view of another embodiment of a hybrid atraumatic head 14G which is a combination of the atraumatic heads 14D and 14F shown in FIGS. 11 and 13, respectively.

FIG. 14 illustrates an alternate embodiment of a hybrid atraumatic head 14G for the guidewire 10 of the present invention shown in FIG. 1. This atraumatic head 14G comprises a housing 200 connected to the distal portion 44C of the core wire 44. The housing 200 supports a distal atraumatic lens 202, which has a hemispherical- or parabolic-shaped exterior surface and is made of similar materials as previously described for lens 46. The housing 200 comprises a cylindrically-shaped proximal section 200A meeting an enlarged diameter cylindrically-shaped distal section 200B at an annular step 200C. The housing distal section 200B has an annular rim 200D that surrounds a recess 204 leading to an axial inlet 206. An off-set bore 208 extends through the housing 200 from a proximal face 200E to the axial inlet 206. A reduced diameter proximal portion of the atraumatic lens 202 is fitted into the recess 204 leading to the axial inlet 206 to connect the hybrid atraumatic head 14G to the housing 200.

The housing 200 also has an annular tapered sidewall 200F that leads to a lateral inlet 210 which extends into the distal section 200B of the housing. The lateral inlet 210 meets the axial inlet 206 with both inlets 206, 210 being open to the off-set bore 208. The printed circuit board (PCB) 54 resides in the off-set bore 208 to mechanically support the camera chip 16, which is preferably a CMOS or CCD camera chip, and electrically connect the camera chip to the electrical cable 56. A transparent coating 60 protects the camera chip 16 from damage.

A prism-shaped mirror 212 is fitted into a proximal portion of the axial inlet 206. Then, an axially aligned collimated gradient-index (GRIN) lens 214 is seated in a distal portion of the axial inlet 206 abutting an edge of the prism-shaped mirror 212. The mirror 212 is angles at 45° to the plane of the collimated image of the GRIN lens 214. The distal atraumatic lens 202 is made of a glass that causes exemplary incoming light rays 216, 218 and 220 to refract to a focal point 222 inside the lens 202. This point is the distal focal point of the axial GRIN lens 214. The light rays 216, 218 and 220 then disperse past the focal point 222 as they enter the GRIN lens 214.

Light ray 216 is shown entering the distal atraumatic lens 202 along the longitudinal axis A-A. This light ray 216 travels along that axis through the atraumatic lens 202, the axial GRIN lens 214 and a proximal void space 216 before impinging on the prism-shaped mirror 212 which reflects the light ray 90° onto a distal portion of the camera chip 16.

Light ray 220 enters the atraumatic lens 202 spaced from the longitudinal axis A-A to then refract through the focal point 222 before entering the axial GRIN lens 214 where it bends through the radial refractive index of that lens to then enter the proximal void space 216 aligned substantially parallel to but spaced from light ray 216 traveling along the longitudinal axis A-A. Light ray 220 then impinges on the prism-shaped mirror 212 to reflect 90° onto the distal portion of the camera chip 16.

Light ray 218 is shown entering the atraumatic lens 202 aligned along the longitudinal axis A-A and between light rays 216 and 220. The atraumatic lens 202 refracts this light ray 218 through the focal point 222 before it enters the axial GRIN lens 214 where the light ray bends through the gradient of refractive index of that lens to then enter the proximal void space 216 aligned substantially parallel to, but between light rays 216 and 220. Light ray 218 then impinges on the prism-shaped mirror 164 where it is reflected 90° onto a distal portion of the camera chip 16.

A lateral GRIN lens 224 resides in the lateral inlet 210 with its inner face 224A aligned with the off-set bore 208. An outer face 224B of the lateral GRIN lens 224 supports a lateral atraumatic lens 226 which resides in the annular taper 200F. The lateral atraumatic lens 226 has a hemispherical- or parabolic-shaped exterior surface and is made of similar materials as previously described for lens 46. The lateral traumatic lens 226 causes exemplary incoming light rays 228, 230 and 232 to refract to a focal point 234 inside the lateral lens 226. This point is the distal focal point of the lateral GRIN lens 224. The light rays 228, 230 and 232 disperse past the focal point 234 as they enter the GRIN lens 224.

Light ray 228 is shown entering the lateral lens 226 along a longitudinal axis B-B. This light ray 228 travels along that axis through the atraumatic lens 226 and the lateral GRIN lens 224 before impinging on a distal portion of the camera chip 16.

Light ray 232 enters the atraumatic lens 236 spaced from the longitudinal axis B-B to then refract through the focal point 234 before entering the lateral GRIN lens 224 where it bends through the radial refractive index of that lens to then align substantially parallel to but spaced from light ray 228 traveling along the longitudinal axis B-B. Light ray 232 then impinges on the distal portion of the camera chip 16.

Light ray 230 is shown entering the atraumatic lens 226 aligned along the longitudinal axis B-B and between light rays 228 and 232. The lateral atraumatic lens 226 refracts this light ray 230 through the focal point 234 before it enters the lateral GRIN lens 224 where the light ray bends through the gradient of refractive index of that lens to then align substantially parallel to, but between light rays 228 and 232. Light ray 194 then impinges on the distal portion of the camera chip 16.

Figure 15:
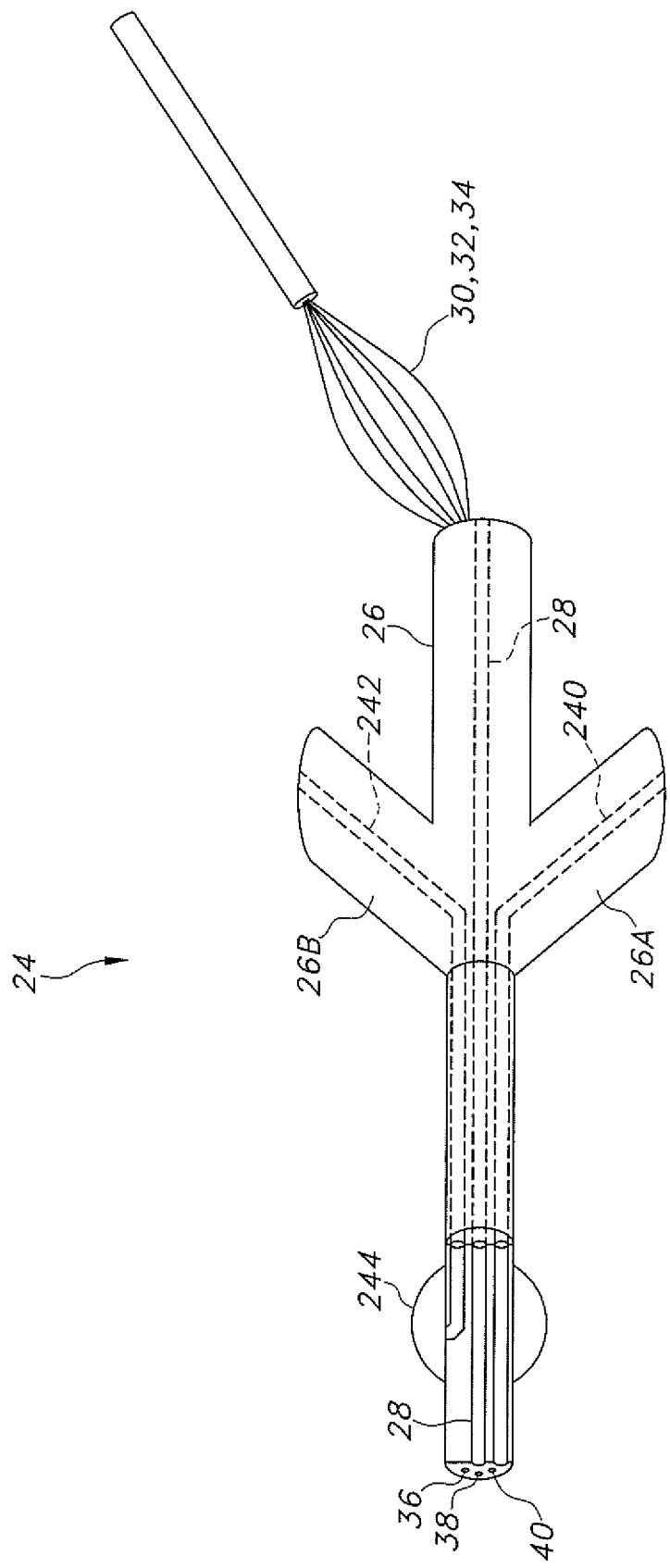
FIG. 15 is a schematic view of the catheter 24 for the guidewire and catheter system 10 shown in FIGS. 1 and 2.

FIG. 15 is a schematic view of the catheter 24 shown in FIGS. 1 and 2. As previously described, the cylindrically-shaped sidewall 26 of the catheter 24 defines an axially-extending primary lumen 28 and supports a plurality of optical fibers, for example optical fibers 30, 32 and 34. The optical fibers 30, 32 and 34 are evenly spaced about the primary lumen 28 and extend to respective light-emitting lenses 36, 38 and 40, which are configured to illuminate the vasculature 42 of a patient as the guidewire and catheter system 10 of the present invention is used in a medical procedure. Preferably, the catheter 24 is formed of a biocompatible and biostable primary polymeric material. Suitable materials include thermoplastics such as Nylon, PEBAX®, PET, thermosets such as silicone, polytetrafluoroethylene (PTFE), polyimide and composites such as liquid crystal polymers. If desired, these materials can be glass-filled or filled with a radiopaque material. Examples of radiopaque fillers are barium sulphate, bismuth subcarbonate, and tungsten.

In addition to the axially-extending primary lumen 28, which is sized to receive the guidewire 12 during a medical procedure, the catheter 24 also has several secondary lumens. A first wing 26A connected to the sidewall 26 provides an auxiliary lumen 240 that is used for any one of many purposes including providing saline, medicine or a secondary medical instrument to the body tissue of interest. A second wing 26B connected to the sidewall 26 provides an inflation lumen 242 that is used to inflate a balloon 244 secured to the catheter 24 a short distance proximal a distal end of the catheter.

A further embodiment of the catheter 24 include push-pull wires extending from a handle assembly connected to a proximal end of the catheter to a distal end thereof. Manipulation of the handle assembly moves the push-pull wires to selectively deflect the distal end of the catheter.

In Use

During a medical procedure, the guidewire 12 is inserted into the vasculature 42 (FIG. 1) of a patient through an incision into an accessible artery, such as the femoral artery. The catheter 24 is then moved over the guidewire 12 by aligning the primary lumen 28 with the guidewire. Then, the guidewire 12 is connected to the proximal connector 18 so that the controller 20 can send electrical power to the camera chip 16 in the atraumatic head 14. The light-emitting lens 36, 38 and 40 of the catheter 24 are used to visualize the path the guidewire is taking through the vasculature 42 before the surgeon begins studying a specific area of interest. In a preferred embodiment, each optical fiber 30, 32 and 34 in connected to a different wavelength spectrum coming from the controller 20 to allow multispectral illumination by the respective light-emitting lenses 36, 38 and 40 of a target tissue. Blood can be cleared intermittently along the path by inflating the balloon 244 with saline through lumen 242 and by flowing a saline solution through auxiliary lumen 240 into the vessel and around the tissue under inspection.

Once powered, the camera chip 16 is configured to send a video feedback to the controller 20 electrically connected to the display 22 to show the surgeon the vasculature tissue immediately adjacent to the atraumatic head. The inverted image from the camera chip 16 is converted to a visual image oriented to the surgeon's perspective of the tissue. Also, the controller 20 is programmed to process the image feedback from the camera chip to provide an in-vivo hyperspectral image (HSI) for disease diagnosis of the tissue of interest and image-guided surgery. HSI acquires a three-dimensional data set called a hypercube with two spatial dimensions (the image) and one spectral dimension (the light wavelength).

Moreover, the controller 20 is programmed to cause the optical fibers 30, 32 and 34 optically connected light-emitting lenses 36, 38 and 40 to emit different wavelengths consecutively to illuminate the tissue with the different wavelengths. For each wavelength illuminating the tissue, the image is captured by the camera chip 16 in a single exposure and the controller 20 then steps through the wavelengths to complete the data set.

In that respect, light delivered to biological tissue undergoes multiple scatterings because of the inhomogeneity of biological structures and absorption primarily in haemoglobin, melanin, and water as the light propagates through the tissue. The absorption, fluorescence, and scattering characteristics of tissue change during the progression of a disease. Therefore, the reflected, fluorescent, and transmitted light from tissue in the form of a hyperspectral image carries quantitative diagnostic information about tissue pathology. For example, vulnerable plaques constitute a risk for serious heart problems, and are difficult to identify using existing methods. Hyperspectral imaging combines spectral- and spatial information to provide a precise optical characterization of atherosclerotic lesions.

Thus, the various forward viewing atraumatic heads described herein above, namely atraumatic head 14 (FIG. 7), atraumatic head 14A (FIG. 7B), atraumatic head 14B (FIG. 7C), atraumatic head 14C (FIG. 10), atraumatic head 14D (FIG. 11) and atraumatic head 14E (FIG. 12) provide the surgeon with a real-time hyperspectral image of the vasculature as the medical procedure, such as placing a stent or other medical device inside the body, is being done. Additionally, the side viewing atraumatic head 14 shown in FIG. 13 provides the surgeon with a real-time hyperspectral image of the sidewall of the vasculature somewhat proximal the atraumatic head, if that is desired. Further, if desired, the hybrid atraumatic head 14G shown in FIG. 14 provides the surgeon with both a forward-looking hyperspectral image and a sidewall hyperspectral image of the vasculature during the medical procedure.

Once the medical procedure is completed, the saline solution is withdrawn from the saline lumen 242 to deflate the balloon 244. The light-emitting lenses 36, 38 and 40 are turned off and the guidewire and catheter system 10 is withdrawn from the vasculature. The guidewire 12 is then disconnected from the proximal connector 18 for disposal or possible cleaning for re-use. The catheter 24 and connector 18 can also be disposed of or cleaned for re-use. The controller 20 and display 22 can be used for many surgical procedures.

It is appreciated that various modifications to the inventive concepts described herein may be apparent to those skilled in the art without departing from the scope of the present invention as defined by the hereinafter appended claims.

What is claimed is:

1. A guidewire, comprising:
a) a core wire extending along a longitudinal axis from a core wire proximal end to a core wire distal portion having a core wire distal end;
b) a housing connected to the core wire distal end;
c) a coil spring connected to the core wire distal portion and the housing, wherein the core wire distal end connected to the housing resides inside the coil spring;
d) a printed circuit board (PCB) electrically connected to a camera chip, wherein the PCB is connected to the housing;
e) a power cable extending along the core wire to the PCB to thereby provide electrical power to the camera chip; and
f) an atraumatic lens supported by the housing, wherein the camera chip resides between the atraumatic lens and the housing so that light rays entering the atraumatic lens are refracted to a focal plane aligned along a distal face of the camera chip.

2. The guidewire of claim 1, wherein the atraumatic lens has a hemispherical- or parabolic-shaped exterior surface.

3. The guidewire of claim 1, wherein the atraumatic lens is made from an optical glass selected from silicon dioxide, fused silica and quartz, zinc selenide, zinc sulfide, germanium, sapphire, calcium fluoride, and barium fluoride, or the atraumatic lens is made from an optical plastic selected from silicone elastomers, poly methyl methacrylate, polycarbonate, and polystyrene.

4. The guidewire of claim 1, wherein the focal plane aligned along the distal face of the camera chip is oriented perpendicular to the longitudinal axis of the core wire, and wherein the atraumatic lens has a proximal-facing hemispherical-, parabolic- or disc-shaped surface that defines a respective hemispherical-, parabolic- or disc-shaped void space so that light rays refracted by the atraumatic lens are further refracted by the void space before impinging on the focal plane aligned along the distal face of the camera chip.

5. The guidewire of claim 1, further comprising a proximal lens having a relatively lower dispersion, the proximal lens having a distal-facing surface and a proximal-facing surface forming a void space, wherein the atraumatic lens has a relatively higher dispersion and a proximal-facing surface that is optically coupled to the distal-facing surface of the proximal lens, and wherein the camera chip is axially aligned between the proximal lens and the housing.

6. The guidewire of claim 5, wherein the proximal-facing surface of the atraumatic lens has a concave shape and wherein the distal-facing surface of the proximal lens has a convex shape that is optically coupled to the concave proximal-facing surface of the atraumatic lens so that a light ray entering the atraumatic lens is refracted into its component wavelengths which are further refracted by the proximal lens and then refracted again by the void space to converge at a common focal point on the focal plane aligned along the distal face of the camera chip.

7. The guidewire of claim 5, wherein the proximal lens is a collimated gradient-index (GRIN) lens, and the housing supports a prism that resides between the proximal collimated GRIN lens and the camera chip, and wherein light rays refracted by the atraumatic lens are further refracted by the proximal collimated GRIN lens and then reflected by the prism to impinge on the camera chip.

8. The guidewire of claim 7, wherein the atraumatic lens has a proximally-facing hemispherical-, parabolic- or disc-shaped void space facing the proximal collimated GRIN lens.

9. The guidewire of claim 5, wherein the atraumatic lens is made of crown glass and the proximal lens is made of flint glass.

10. The guidewire of claim 1, wherein the housing has a distally facing recess, and wherein the PCB and camera chip are nested in the housing recess.

11. The guidewire of claim 1, wherein the core wire has a distal tapered portion extending to the distal portion having the distal end, and wherein the distal tapered portion of the core wire connected to the housing resides inside the coil spring.

12. The guidewire of claim 1, wherein a protective coating resides between the atraumatic lens and the camera chip.

13. The guidewire of claim 1, further comprising:
 a) an axially aligned collimated GRIN lens having a distal-facing surface that is optically connected to a proximal-facing surface of the atraumatic lens;
 b) a prism residing between a proximal-facing surface of the axially aligned GRIN lens and the camera chip;
 c) a lateral atraumatic lens supported by the housing in a lateral inlet extending into the housing, wherein the lateral atraumatic lens has a first surface facing the longitudinal axis extending through the core wire; and
 d) a lateral collimated GRIN lens supported by the housing, wherein the lateral collimated GRIN lens has a second surface that is optically coupled to the first surface of the lateral atraumatic lens and a third surface facing the camera chip,
 e) wherein axially incoming light rays refracted by the atraumatic lens are further refracted by the axially aligned collimated GRIN lens and then reflected by the prism to impinge on a distal portion of the camera chip, and
 f) wherein laterally incoming light rays refracted by the lateral atraumatic lens are further refracted by the lateral collimated GRIN lens before impinging on a proximal portion of the camera chip.

14. A guidewire, comprising:
 a) a core wire extending along a longitudinal axis from a core wire proximal end to a core wire distal portion having a core wire distal end;
 b) a housing connected to the core wire distal end, wherein the housing has a lateral inlet extending to an axial bore;
 c) a coil spring connected to the core wire distal portion and the housing, wherein the core wire distal end connected to the housing resides inside the coil spring;
 d) a printed circuit board (PCB) electrically connected to a camera chip, wherein the camera chip and PCB reside in the axial bore of the housing with a focal plane of the cameral chip aligned parallel to the longitudinal axis of the core wire;
 e) a power cable extending along the core wire to the PCB to thereby provide electrical power to the camera chip;
 f) a distal atraumatic lens supported by the housing, wherein the distal atraumatic lens has a proximal-facing surface;
 g) an axially aligned collimated gradient-index (GRIN) lens having a proximal-facing surface and a distal-facing surface, wherein the distal-facing surface of the axially aligned collimated GRIN lens is optically connected to the proximal-facing surface of the distal atraumatic lens;
 h) a prism residing between the proximal-facing surface of the axially aligned GRIN lens and the camera chip;
 i) a lateral atraumatic lens supported by the housing in the lateral inlet, wherein the lateral atraumatic lens has a first surface facing the longitudinal axis extending through the core wire; and
 j) a lateral collimated GRIN lens supported by the housing, wherein the lateral collimated GRIN lens has a second surface that is optically coupled to the first surface of the lateral atraumatic lens and a third surface facing the camera chip,
 k) wherein axially incoming light rays refracted by the distal atraumatic lens are further refracted by the axially aligned collimated GRIN lens and then reflected by the prism to impinge on a distal portion of the camera chip, and
 l) wherein laterally incoming light rays refracted by the lateral atraumatic lens are further refracted by the lateral collimated GRIN lens before impinging on a proximal portion of the camera chip.

15. The guidewire of claim 14, wherein the distal and lateral atraumatic lens each have a hemispherical- or parabolic-shaped exterior surface.

16. The guidewire of claim 14, wherein the distal and lateral atraumatic lens are individually made from an optical glass selected from silicon dioxide, fused silica and quartz, zinc selenide, zinc sulfide, germanium, sapphire, calcium fluoride, and barium fluoride, or the atraumatic lens is made from an optical plastic selected from silicone elastomers, poly methyl methacrylate, polycarbonate, and polystyrene.

17. The guidewire of claim 14, wherein the core wire has a distal tapered portion extending to the distal portion having the distal end, and wherein the distal tapered portion of the core wire connected to the housing resides inside the coil spring.

18. A medical system, comprising:
 a) guidewire, comprising:
  i) a core wire extending along a longitudinal axis from a core wire proximal end to a core wire distal portion having a core wire distal end;
  ii) a housing connected to the core wire distal end;
  iii) a printed circuit board (PCB) electrically connected to a camera chip, wherein the PCB is connected to the housing;
  iv) a power cable extending along the core wire to the PCB to thereby provide electrical power to the camera chip; and
  v) an atraumatic lens supported by the housing, wherein the camera chip resides between the atraumatic lens and the housing so that light rays entering the atraumatic lens are refracted to a focal plane aligned along a distal face of the camera chip; and
 b) a proximal connector powered by a controller that is wired to a visual display, wherein the proximal end of the guidewire is detachably connectable to the proximal connector to enable the controller to provide electrical power to the camera chip;

c) a catheter, comprising:
  i) a sidewall defining an axially-extending primary lumen; and
  ii) a plurality of optical fibers extending through the sidewall to respective light-emitting lenses,
  iii) wherein the plurality of optical fibers are optically connected to the controller to provide optical power to the respective light-emitting lenses, d) wherein, with the guidewire inserted into the vasculature of a patient, the guidewire is configured to be received in the primary lumen of the catheter to connect the catheter to the guidewire, and wherein the proximal end of the guidewire is then connectable to the proximal connector to enable the controller to provide electrical power to the camera chip so that a visual image of the vasculature illuminated by the light-emitting lenses of the catheter is sent to the visual display via the controller during the medical procedure.

19. The medical system of claim 18, wherein the catheter has at least one auxiliary lumen, and wherein the catheter supports an inflatable balloon in open communication with the auxiliary lumen.

20. The medical system of claim 18, wherein the controller is programmable to process an image feedback from the camera chip to provide an in-vivo hyperspectral image (HSI) of the vasculature.

21. The medical system of claim 18, wherein the proximal controller is programmable to emit different wavelengths consecutively that are input to the plurality of optical fibers optically connected to the respective light-emitting lens to illuminate the vasculature with the different wavelengths.

* * * * *